(12) United States Patent
Chang et al.

(10) Patent No.: US 10,557,141 B2
(45) Date of Patent: Feb. 11, 2020

(54) PLANT TRANSFORMATION METHOD

(75) Inventors: Yin-Fu Chang, Carrboro, NC (US); Aparna Sri Vanguri, Raleigh, NC (US); Leslie Grist, Raleigh, NC (US); Holly Tuttle, Durham, NC (US); Hai Ping Hong, Cary, NC (US); Paula Olhoft, Morrisville, NC (US)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 777 days.

(21) Appl. No.: 14/234,007

(22) PCT Filed: Jul. 20, 2012

(86) PCT No.: PCT/IB2012/053705
§ 371 (c)(1),
(2), (4) Date: Apr. 21, 2014

(87) PCT Pub. No.: WO2013/014585
PCT Pub. Date: Jan. 31, 2013

(65) Prior Publication Data
US 2014/0237688 A1  Aug. 21, 2014

Related U.S. Application Data

(60) Provisional application No. 61/510,513, filed on Jul. 22, 2011.

(30) Foreign Application Priority Data

Jul. 22, 2011 (EP) .................................... 11175038

(51) Int. Cl.
C12N 15/82 (2006.01)

(52) U.S. Cl.
CPC ..... *C12N 15/8201* (2013.01); *C12N 15/8205* (2013.01)

(58) Field of Classification Search
None
See application file for complete search history.

(56) References Cited

U.S. PATENT DOCUMENTS

| | | | |
|---|---|---|---|
| 2,753,277 A | 7/1956 | Smithers | |
| 4,975,374 A | 12/1990 | Goodman et al. | |
| 5,010,686 A * | 4/1991 | Rivest | A01G 31/02 47/62 C |
| 7,022,896 B1 | 4/2006 | Weeks et al. | |
| 8,071,383 B2 | 12/2011 | Arias et al. | |
| 9,040,774 B2 * | 5/2015 | Ivashuta | C12N 15/111 800/285 |
| 2003/0046733 A1 | 3/2003 | Dias | |
| 2006/0260012 A1 | 11/2006 | Khan | |
| 2009/0049567 A1 | 2/2009 | Olhoft et al. | |
| 2010/0287641 A1 | 11/2010 | McElver et al. | |

FOREIGN PATENT DOCUMENTS

| | | |
|---|---|---|
| CN | 1668744 A | 9/2005 |
| CN | 101405394 A | 4/2009 |
| CN | 101736028 | 6/2010 |
| EP | 0333033 | 9/1989 |
| EP | 0601092 | 6/1994 |
| WO | WO 1993005163 | 4/1993 |
| WO | WO 1994007356 | 4/1994 |
| WO | WO 1997021326 | 6/1997 |
| WO | WO 1997023126 | 7/1997 |
| WO | WO 1999018223 | 4/1999 |
| WO | WO 2000042207 | 7/2000 |
| WO | WO 2000056904 | 9/2000 |
| WO | WO 2001044459 | 6/2001 |
| WO | WO 2001087070 | 11/2001 |
| WO | WO 2002066599 | 8/2002 |
| WO | WO 2003017752 | 3/2003 |
| WO | WO 2003060133 | 7/2003 |
| WO | WO 2004005516 | 1/2004 |
| WO | WO 2005090584 | 9/2005 |
| WO | WO 2005121345 | 12/2005 |
| WO | WO 2006015376 | 2/2006 |
| WO | WO 2007054555 | 5/2007 |
| WO | WO 2007107516 | 9/2007 |
| WO | WO 2008077570 | 7/2008 |

(Continued)

OTHER PUBLICATIONS

Piqueras et al (Explants Used for the Generation of Transgenic Plants. C. Kole et al. (eds.), Transgenic Crop Plants, p31-56, Springer-Verlag Berlin Heidelberg 2010).*
Olhoft et al (A novel Agrobacterium rhizogenes-mediated transformation method of soybean [*Glycine max* (L.) Merrill] using primary-node explants from seedlings. In Vitro Cell. Dev. Biol.—Plant 43:536-549, 2007).*
Garcia-Luis et al (Explant Orientation and Polarity Determine the Morphogenic Response of Epicotyl Segments of Troyer Citrange. Annals of Botany 84: 715-723, 1999).*
Dan et al (Development of Efficient Plant Regeneration and Transformation System for Impatiens Using Agrobacterium tumefaciens and Multiple Bud Cultures as Explants. BMC Plant Biology 10:165, p1-12, 2010).*
Ahn et al (High-frequency plant regeneration through adventitious shoot formation in castor (*Ricinus communis* L.). In Vitro Cell.Dev. Biol.—Plant. 43:9-15, 2007).*
Molnar et al (Small Silencing RNAs in Plants Are Mobile and Direct Epigenetic Modification in Recipient Cells. Science, vol. 328, 872-875, May 14, 2010) (Year: 2010).*

(Continued)

*Primary Examiner* — Medina A Ibrahim
*Assistant Examiner* — Wayne Zhong
(74) *Attorney, Agent, or Firm* — Marshall, Gerstein & Borun LLP

(57) ABSTRACT

The present invention relates to an improved method of producing a transgenic plant. Said method comprises, inter alia, the steps of a) providing a wounded transformable explant comprising a hypocotyl or a portion thereof, at least one cotyledon and wounded tissue, b) transforming cells comprised by said explant, and c) transferring said explant to a growing medium, comprising at least one selection compound for a selectable marker, by inserting the hypocotyl of said explant into said growing medium. Moreover, the present invention relates to a plant obtainable by the method according to the present invention.

19 Claims, 4 Drawing Sheets

(56) References Cited

FOREIGN PATENT DOCUMENTS

Figure 1:

| WO | WO 2008112044 | 9/2008 | | |
|---|---|---|---|---|
| WO | WO 2008124495 | 10/2008 | | |
| WO | WO 2010146046 | 12/2010 | | |
| WO | WO-2010146046 A1 | * 12/2010 | ............. | A01G 31/00 |
| WO | WO 2010146046 A1 | * 12/2010 | ............. | A01G 31/00 |

OTHER PUBLICATIONS

Duan et al., "Comparison and optimization of the agrobacterium-mediated transformation of soybean by using cotyledonary node and hypocotyl explants", Soybean Science, 29(4):590-593 (2010).
Office Action, Chinese patent application No. 201280036070.1, dated Dec. 31, 2014.
Aragão et al., "Inheritance of Foreign Genes in Transgenic Bean (Phaseolus vulgaris L.) Co-transformed via Particle Bombardment," Theor Appl Genet, vol. 93, (1996), pp. 142-150.
Aragão et al., "Selection of Transgenic Meristematic Cells Utilizing a Herbicidal Molecular Results in the Recovery of Fertile Transgenic Soybean [Glycine max (L.) Merril] Plants at a High Frequency," Theor Appl Genet, vol. 101, (2000), pp. 1-6.
Bablak et al., "Plant Regeneration and Micropropagation of Brachypodium disfachyon," Plant Cell, Tissue and Organ Culture, vol. 42, (1995), pp. 97-107.
Behrens et al., "Dicamba Resistance: Enlarging and Preserving Biotechnology-Based Weed Management Strategies," Science, vol. 316, (2007), pp. 1185-1188.
Birch, "Plant Transformation: Problems and Strategies for Practical Application," Annu. Rev. Plant Physiol. Plant Mol, Biol., vol. 48, (1997), pp. 297-326.
Cardoza and Stewart, Jr., "Agrobacterium-Mediated Transformation of Canola," Transgenic Crops of the World—Essential Protocols, I.S. Curtis (ed.), (2004), pp. 379-387.
Chilton et al., "Stable Incorporation of Plasmid DNA into Higher Plant Cells: The Molecular Basis of Crown Gall Tumorigenesis," Cell, vol. 11, (1977), pp. 263-271.
Christiansen et al., "A Rapid and Efficient Transformation Protocol for the Grass Brachypodium distachyon," Plant Cell Rep, vol. 23, (2005), pp. 751-758.
Clough and Bent, "Floral Dip: A Simplified Method for Agrobacterium-mediated Transformation of Arabidopsis thaliana," The Plant Journal, vol. 16, No. 6, (1998), pp. 735-743.
De Block et al., "Transformation of Brassica napus and Brassica oleracea Using Agrobacterium tumefaciens and the Expression of the bar and neo Genes in the Transgenic Plants," Plant Physiol, vol. 91, (1989), pp. 694-701.
Estrada-Navarrete et al., "Fast, Efficient and Reporducible Genetic Transformation of Phaseolus spp. by Agrobacterium rhizogenes," Nature Protocols, vol. 2, No. 7, (2007), pp. 1819-1824.
Finer and Nagasawa, "Development of an Embryogenic Suspension Culture of Soybean (Glycine max Merrill.)," Plant Cell, Tissue and Organ Culture, vol. 15, (1988), pp. 125-136.
Finer, "Apical Proliferation of Embryogenic Tissue of Soybean [Glycine max (L.) Merrill]," Plant Cell Reports, vol. 7, (1988), pp. 238-241.
Fraley et al., "Expression of Bacterial Genes in Plant Cells," Proc. Natl. Acad. Sci. USA, vol. 80, (1983), pp. 4803-4807.
Gelvin, "Agrobacterium-Mediated Plant Transformation: The Biology Behind the "Gene-Jockeying" Tool," Microbiology and Molecular Biology Reviews, vol. 67, No. 1, (2003), pp. 16-37.
Graves and Goldman, "The Transformation of Zea mays Seedlings with Agrobacterium tumefaciens," Plant Molecular Biology, vol. 7, (1986), pp. 43-50.

Han et al., "Optimization of Regeneration System from Cotyledonary Nodes of Soybean and Agrobacterium-mediated Transformation," Journal of Northeast Agricultural University, vol. 41, No. 2, (2010), pp. 1-13.
Hinchee et al., "Production of Transgenic Soybean Plants using Agrobacterium-mediated DNA Transfer," Biotechnology, vol. 6, (1988), pp. 915-922.
Horsch et al., "A Simple and General Method for Transferring Genes into Plants," Science, vol. 227, (1985), pp. 1229-1231.
International Preliminary Report on Patentability, issued in PCT/IB2012/053705, dated Feb. 6, 2014.
International Search Report, issued in PCT/IB2012/053705, dated Nov. 29, 2012.
Jonoubi et al., "Efficient Regeneration of Brassica napus L. Hypocotyls and Genetic Transformation by Agrobacterium tumefaciens," Biologic Plantarum, vol. 49, No. 2, (2005), pp. 175-180.
Ko et al., "A Partially Disarmed vir Helper Plasmid, pKYRT1, in Conjunction with 2,4-dichlorophenoxyactic Acid Promotes Emergence of Regenerable Transgenic Somatic Embryos from Immature Cotyledons of Soybean," Planta, vol. 218, (2004), pp. 536-541.
Ko et al., "Two Critical Factors are Required for Efficient Transformation of Multiple Soybean Cultivars: Agrobacterium Strain and Orientation of Immature Cotyledonary Explant," Theor Appl Genet, vol. 107, (2003), pp. 439-447.
Liu and Wei, "Research Progress in Genetic Transformation of Soybean," Journal of Plant Physiology and Molecular Biology, vol. 31, No. 2, (2005), pp. 126-134.
Moralejo et al., "Generation of Transgenic Eucalyptus globulus Plantlets Through Agrobacterium tumefaciens Mediated Transformation," Aust. J. Plant Physiol., vol. 25, (1998), pp. 207-212.
Olhoft and Somers, "L-Cysteine Increases Agrobacterium-mediated T-DNA Delivery into Soybean Cotyledonary-Node Cells," Plant Cell Rep., vol. 20, (2001), pp. 706-711.
Olhoft et al., "Efficient Soybean Transformation Using Hygromycin B Selection in the Cotyledonary-Node Method," Planta, vol. 216, (2003), pp. 723-735.
Olhoft et al., "Soybean (Glycine max) Transformation Using Mature Cotyledonary Node Explants," Methods in Molecular Biology, vol. 343, (2006), pp. 385-396.
Olhoft et al., "The Role of Thiol Compounds in Increasing Agrobacterium-mediated Transformation of Soybean Cotyledonary-Node Cells," Plant Cell Rep., vol. 20, (2001), pp. 731-737.
Parrott et al., "Recovery of Primary Transformants of Soybean," Plant Cell Reports, vol. 7, (1989), pp. 615-617.
Tzfira et al., "Agrobacerium rhizogenes-mediated DNA Transfer in Pinus halopensis Mill.," Plant Cell Reports, vol. 16, (1996), pp. 26-31.
Wang et al., "Development of a Novel Agrobacterium-mediated Transformation Method to Recover Transgenic Brassica napus Plants," Plant Cell Rep., vol. 22, (2003), pp. 274-281.
Wang et al., "Maize (Zea mays) Genetic Transformation by Co-cultivating Germinating Seeds with Agrobacterium tumefaciens," Biotechnol. Appl. Biochem., vol. 46, (2007), pp. 51-55.
Weeks et al., "Development of an in planta Method for Transformation of Alfalfa (Medicago sativa)," Transgenic Res, vol. 17, (2008), pp. 587-597.
Wright et al., "Initiation and Propagation of Glycine max L. Merr.: Plants from Tissue-Cultured Epicotyls," Plant Cell, Tissue and Organ Culture, vol. 8, (1987), pp. 83-90.
Xue et al., "A Multi-Needle-Assisted Transformation of Soybean Cotyledonary Node Cells," Biotechnol Lett, vol. 28, (2006), pp. 1551-1557.
Yan et al., "Agrobacterium tumefaciens—Mediated Transformation of Soybean [Glycine max (L.) Merrill.] Using Immature Zygotic Cotyledon Explants," Plant Cell Reports, vol. 19, (2000), pp. 1090-1097.
Zhao et al., "Technique Flow and Key Operation Points of Agrobacterium-mediated Genetic Transformation of Soybean Cotyledonary Node," Soybean Science, vol. 30, No. 3, (2011), 20 pages.

* cited by examiner

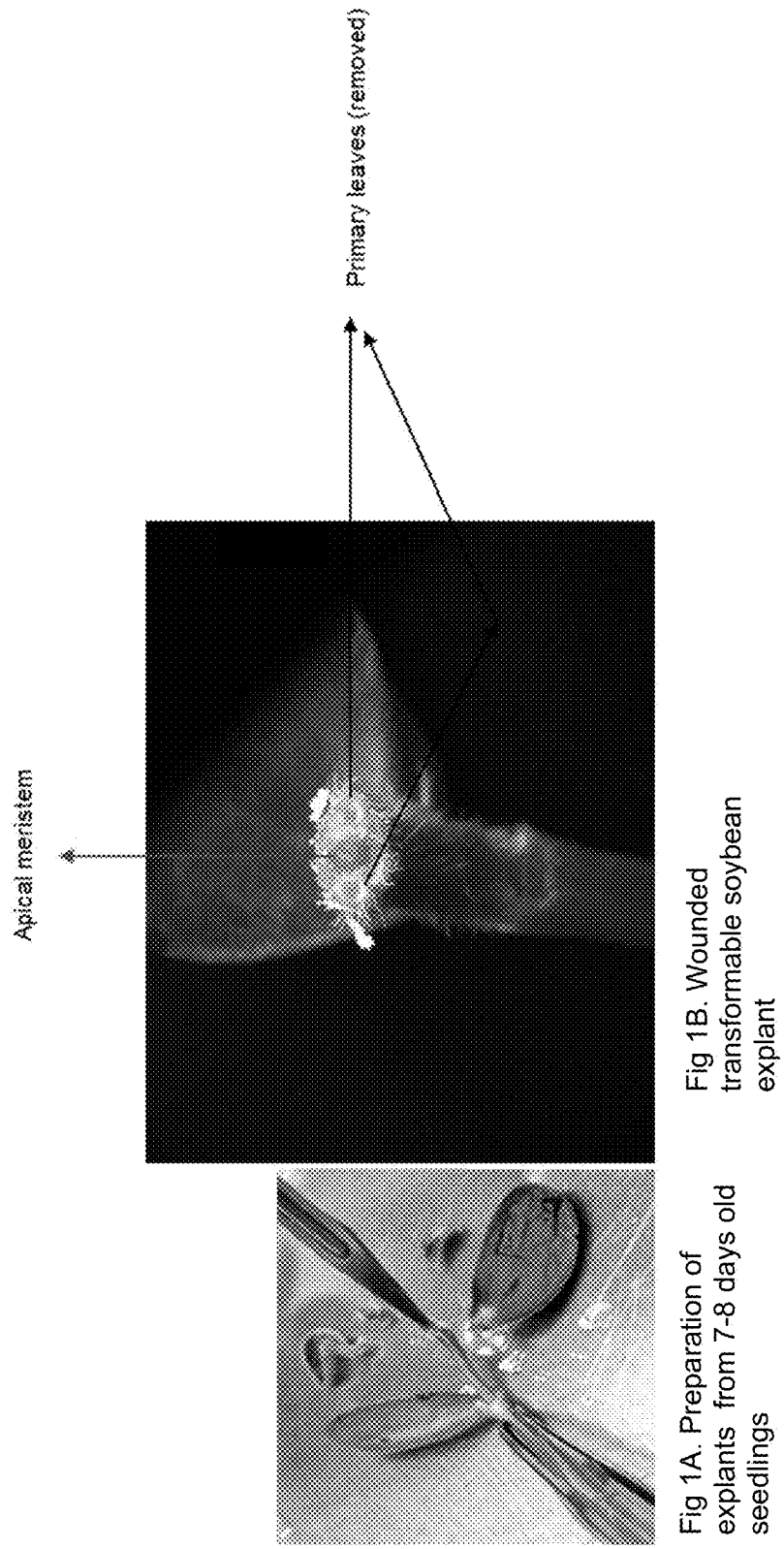

Fig 1C. Co-cultivation with Agrobacterium

Figure 2:
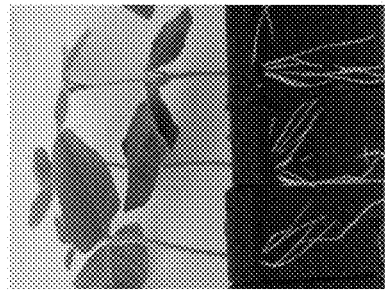
Figure 2:
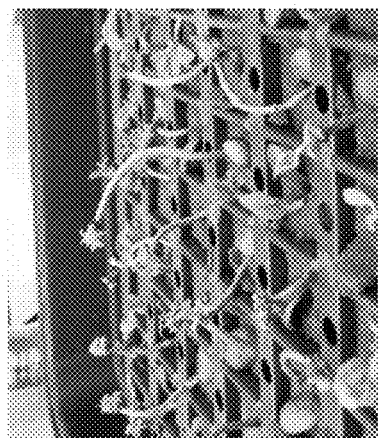

Fig 2B. Separation and rooting of elongated shoots

Fig 2A. Explants with emerging shoots (transferred from shoot induction medium).

PLANT TRANSFORMATION METHOD

This application is a National Stage application of International Application No. PCT/IB2012/053705, filed Jul. 20, 2012, which claims the benefit of U.S. Provisional Application No. 61/510,513, filed Jul. 22, 2011. This application also claims priority under 35 U.S.C. § 119 to European Patent Application No. 11175038.6, filed Jul. 22, 2011.

The present invention relates to a method of producing a transgenic plant. Said method comprises, inter alia, the steps of a) providing a wounded transformable explant comprising a hypocotyl or a portion thereof, at least one cotyledon and wounded tissue, b) transforming cells comprised by said explant, and c) transferring said explant to a growing medium, comprising at least one selection compound for a selectable marker. Moreover, the present invention relates to a plant obtainable by the method according to the present invention.

Agrobacterium-mediated plant transformation, first described for tobacco in 1984, is now widely used for introduction of genes into plants for purposes of basic research as well as for generation of commercially used transgenic crops. Plants which can be successfully transformed include most major economic crops, vegetables, ornamental, medicinal, fruit, tree, and pasture plants.

Plant transformation is mostly done by Agrobacterium-mediated plant transformation. Agrobacterium is a naturally occurring pathogenic soil bacterium which is capable of transferring DNA into the genome of plant cells. For Agrobacterium-mediated plant transformation, the gene of interest is placed between the left and right border repeats of Agrobacterium T-DNA (transfer DNA). Afterwards, the T-DNA region containing the gene of interest is stably integrated into the plant genome by using an appropriate plant transformation protocol (for a review see Gelvin, 2003 Microbiol Mol Biol Rev. 67(1): 16-37).

Aside from Agrobacterium-mediated plant transformation, other plant transformation methods exist such as viral transformation, electroporation of plant protoplasts, and particle bombardment.

Generally, plant transformation techniques are based on the same principles. In a first step, the gene of interest is introduced in a suitable transformation vector. The transformation vector harbouring the gene of interest is then introduced into regenerable cells of a target plant. Since only a minor proportion of target cells receive the gene of interest, selection for transformed plant cells among a large excess of untransformed cells is carried out. Moreover, once the gene of interest has been stably introduced into the genome of a host cell, it is essential to establish regeneration conditions in order to regenerate whole plants from a single transformed plant cell (see, e.g., Birch, 1997, Annu. Rev. Plant Physiol. Plant Mol. Biol. 48: 297-326).

One of the simplest available Agrobacterium-based plant transformation methods is "Floral Dip Transformation". Floral Dip is a germline transformation method by which the gene of interest is transformed into cells that give rise to the seeds. This method involves dipping plants (in early flowering stage) in a suspension of Agrobacterium cells (Clough and Bent, 1998, Plant J 16:735-43). A few weeks after dipping, seeds of dipped plants are collected, and the seed population is selected for transformants. The advantage of Floral Dip transformation technique is that it avoids the use of tissue culture and plant regeneration which is cost-intensive and requires trained personnel. Unfortunately, small plant size, short generation time, and a large amount of seeds per plant are prerequisites for Floral Dip. Consequently, this transformation method has only been successfully applied to a few species, mainly for Arabidopsis thaliana (but also with Medicago truncatula and Brassica, see Wang et al 2003. Plant Cell Reports 22: 274-281).

Regeneration of whole transformed plants which are recalcitrant to germline transformation is considered as the bottleneck in plant transformation since regeneration is difficult to achieve, time-consuming, and requires specific equipment.

The first steps of plant regeneration are usually carried out under in vitro conditions, i.e. on a specific nutrient medium under sterile conditions. After transformation of target cells, cell division is induced by specific plant hormones in order to grow a callus from a transformed plant cell. After callus induction, the resulting callus is transferred to a medium allowing shoot induction. The callus is incubated (under in vitro conditions) on said medium until shoots are formed. After shoot formation, the shoot is transferred to a medium that allows for root formation (under in vitro conditions). After root formation, regenerated plantlets (i.e. shoots with roots) are usually transferred from in vitro conditions to ex vitro conditions, mostly to soil under greenhouse conditions. Thus, callus induction, shoot induction and root induction are usually carried out under in vitro conditions.

The current methods for regenerating plants under in vitro conditions, however, have some disadvantages. Regenerating whole plants under in vitro conditions is expensive and requires specific nutrient media, specific equipment and trained personnel. There is, of course, always the risk of contamination (e.g. contamination with fungus). If a tissue culture gets contaminated, the work of weeks or even of months may become worthless.

Without tissue culture, however, plant transformation is challenging since tissue culture
a) allows for selection of transgenic plant cells (and plant shoots, respectively) and
b) simultaneously suppresses growth of bacterial and fungal microorganisms. Without selection, it is difficult to identify plant cells, plant shoots, or plantlets (i.e. plants with shoots and roots) which carry the transgene.

Moreover, the regeneration of transgenic plants is generally a labor-intensive and very time-consuming task. For example, time needed from the isolation of putative transgenic in-vitro Brassica or Brachypodium shoots to ex-vitro adapted, greenhouse ready plants takes 12 weeks to 14 weeks (see e.g. for Brachypodium: Bablak et al (1995) Plant Cell, Tissue and Organ Culture 42: 97-107; or Christiansen et al. (2005) Plant Cell Report 23: 751-758; for Brassica: Cardoza and Stewart (2004), Transgenic crops of the World-Essential Protocols, 379-387; or Jonoubi et al. (2005). Biologia Plantarum 49 (2): 175-180).

Transformation procedures that avoid tissue culture or reduce tissue culture would be valuable, especially for plants which are difficult to regenerate. Scientists have attempted to develop plant transformation procedures that do not require tissue culture, but these attempts have been met with limited success. For example, Graves and Goldman (1986 Plant Mol. Biol. 7: 43-50) reported that Agrobacterium could infect mesocotyl cells of germinating corn seeds, but the resulting transformed plants were chimeras and the transformation efficiency was extremely poor.

The soybean (Glycine max) belongs to the Fabaceae (Leguminosae) family. This plant family is identified by having its seed borne in a legume (pod). The soybean is thought to have originated in China. Wild types of soybeans are viny in nature, which probably is a major reason why soybeans were first introduced in the United States as a hay crop. Introductions from China, Manchuria, Korea and Japan have been important in developing varieties for the United States. Modern breeding efforts to improve the agronomic traits, such as more erect growth, reduced lodging and increased seed size, have been primarily responsible for the development of soybeans into a crop of world-wide importance. The acreage and the proportion of the crop harvested for grain has increased steadily and today soybeans are a major world commodity. With respect to soybean transformation, methods are known which are based on somatic embryogenesis: Embryos are induced from immature soybean cotyledons by placing the explant on high levels of 2,4-D (40 mg/L) and the embryogenic tissues are subsequently proliferated on induction medium (Finer (1988) Plant Cell Rep 7:238-241) or liquid suspension culture (Finer and Nagasawa (1988) Plant Cell Tissue Organ Cult 15:125-136).

Hinchee et al. describes the production of transgenic soybean plants via *Agrobacterium*-mediated transformation. The production of transgenic plants is based on a regeneration protocol in which shoot organogenesis is induced on cotyledons of soybeans (see Hinchee et al. (1988) Nature Biotechnology, 6:915-922).

Also known are methods based on *Agrobacterium*-mediated transformation of zygotic immature cotyledons (Parrott et al. (1989) Plant Cell Rep 7:615-617; Yan et al. (2000) Plant Cell Rep 19:1090-1097; Ko et al. (2003) Theor Appl Genet. 107:439-447). However, in Parrott et al. the three plants produced were chimeric, from a multicellular origin, and did not transmit the transgene to the next generation. Yan et al. (2000) Plant Cell Rep 19:1090-1097 reported a low transformation frequency of 0.03%. The plant produced transmitted the transgene into the next generation, presumably due to the continuous selection of transformed primary embryos for the production of secondary embryos thereby resulting in non-chimeric plants. Recently, Ko et al. (2003) Theor Appl Genet. 107:439-447 has reported the recovery of transgenic plants at 1.7% transformation frequencies, however, the method relies on using a partially disarmed (oncogenic) *Agrobacterium* strain, pKYRT, with a functional TR-DNA sequence in order to stimulate embryogenesis (Ko et al. (2004) Planta 218:536-541). These methods use the immature cotyledons as the target tissue with subsequent proliferation and selection on solid medium.

US2009/0049567 discloses *Agrobacterium*-mediated soybean transformation utilizing meristematic cells of primary or higher leaf nodes as target tissues and subsequent regeneration of the transformed cells into a whole plant.

CN101736028A describes a method for the transformation of soybean independent of tissue culture by transforming the cotyledonary node. Soybean seeds are germinated in vitro or in the fields. After 5 to 7 days, the apical meristem and the meristem are removed from the seedlings. Subsequently the cotyledonary node area was transformed by *Agrobacterium* mediated transformation. After 10 to 15 days the leaves were brushed with a selection compound. The disclosed method however only yielded a relatively low number of transgenic plants (e.g. 127 seedlings were transformed, only 8 transgenic plants were obtained).

Weeks et al. (Transgenic Research (2008), 17, 587-597) describes a method for transforming alfalfa plants. For the transformation, young seedlings were cut at the apical node and vigorously vortexed in an *Agrobacterium* suspension containing an abrasive medium. No selectable marker gene was used in the described method. Therefore, transformation was monitored via PCR and/or histochemic analysis. However, a large number of the regenerated plants were chimeric.

WO00/56904 describes a process for selecting transgenic meristematic cells in cotton, coffee, cocoa, banana or grape plants and the consequent production of transgenic plants. The process comprises the steps of introducing exogenous genes into cells of the apical meristem of embryonic axes or tissues or organs containing meristems of cotton, coffee, cocoa, banana or grape plants; induction of multiple shooting of the cells in the apical meristematic region modified in the preceding step by cultivating their embryonic axes or tissues containing meristems in a medium comprising a multiple shooting inducer; and selecting the transgenic meristematic cells of the apical region by further cultivation of said meristems in a medium containing a molecule which translocate and concentrates in the apical meristematic of embryonic axes of cotton, coffee, cocoa, banana or grape plants.

WO 99/18223 discloses a process for producing transgenic leguminous plants containing exogenous DNA, which comprises the steps of introducing exogenous genes into cells of the apical meristem of embryonic axis of leguminous plants by the biobalistic method; inducing multiple shooting of the cells in the apical meristematic region modified in the preceding step by cultivating their embryonic axis in a medium containing a multiple shooting inducer; and selecting the meristematic cells of the apical region, transformed by further cultivation of said embryonic axis in a medium containing a molecule which concentrates in the apical meristematic region of said leguminous plants embryos.

Aragao et al. discloses the transformation of *Phaseolus vulgaris* by biolistic transformation (Aragão F J L, Barros L M G, Brasileiro A C M, Ribeiro S G, Smith F D, Sanford J C, Faria J C, Rech E L (1996) Inheritance of foreign genes in transgenic bean (*Phaseolus vulgaris* L.) co-transformed via particle bombardment. Theor. Appl. Genet. 93:142-150.). In a further paper, Aragao describes a method to obtain a high frequency of fertile transgenic soybean plants (Aragão F J L, Sarokin L, Vianna G R, Rech E L (2000) Selection of transgenic meristematic cells utilizing an herbicidal molecule results in the recovery of fertile transgenic soybean [*Glycine max* (L.) Merril] plants at high frequency. Theor. Appl. Genet. 101:1-6).

WO 97/23126 discloses a process for the micropropagation of shoots, rooted shoots or seedlings of a woody plant, which comprises cultivating the shoots, rooted shoots or seedlings in an oxygenated liquid medium, the shoots, rooted shoots or seedlings being submerged in the liquid medium.

WO9407356 discloses a method of transforming pomaceous fruit scion or rootstock cultivars with *Agrobacterium tumefaciens*.

Although significant advances have been made in the field of *Agrobacterium*-mediated transformation methods, a need continues to exist for improved methods to facilitate the ease, speed and efficiency of such methods for transformation of plants. Therefore, it was the objective of the present invention to provide an improved method having higher overall efficiency in the process of generation of transgenic soybean plants. This objective is solved by the present invention.

Accordingly, the present invention relates to a method for producing a transgenic plant, comprising the steps of
a) providing a wounded transformable explant, comprising a hypocotyl or a portion thereof, at least one cotyledon, and wounded tissue selected from i. wounded meristematic tissue of a primary or higher leaf node (in particular wounded axillary meristematic tissue of a primary or higher leaf node),
ii. wounded meristematic tissue of the cotyledonary node, and
iii. wounded epicotyl tissue b) transforming cells comprised by the said explant with a polynucleotide comprising at least one plant expression cassette for a selectable marker gene, c) transferring said explant to a growing medium by inserting the hypocotyl, or a portion thereof, of said explant into said growing medium, comprising at least one selection compound for said selectable marker gene, d) allowing said explant to form a shoot, and/or allowing the shoot to elongate, said shoot comprising plant cells comprising said least one plant expression cassette for said selectable marker gene, and e) regenerating a transgenic plant from said shoot.

In the context of the method of the present invention, a transgenic plant shall be produced. The term "transgenic" as used herein, preferably, refers to a cell or plant that has incorporated exogenous DNA sequences. Preferably, said exogenous DNA sequences are stably incorporated into the genome of the transgenic plant or plant cell. Preferably, said exogenous DNA sequences comprise at least one polynucleotide comprising at least one plant expression cassette for a selectable marker gene. Preferably, the expression of the selectable marker gene is regulated by a promoter which allows for expression of said gene in the plant. Such promoters are well known in the art and, preferably, include constitutive promoters, inducible promoters, tissue specific promoters, and development specific promoters. Preferred promoters are e.g. disclosed in US2009/0049567 which herewith is incorporated by reference with respect to its entire disclosure content. The most preferred promoters for the expression of the selectable marker gene are constitutive promoters.

Preferably, the at least one polynucleotide comprising at least one plant expression cassette for a selectable marker gene is not normally present in the plant or plant cell, or is normally present at a different position in the genome of the plant or plant cell. Preferably, the polynucleotide comprising at least one plant expression cassette for a selectable marker gene further comprises a plant expression cassette for an agronomically valuable trait.

The plant to be transformed may be a monocotyledonous plant. Most preferably, the plant to be transformed is a dicotyledonous plant.

Preferably, the dicotyledonous plant is a plant of the family Fabaceae, Solanaceae, Brassicaceae, Chenopodiaceae, Asteraceae, Malvaceae, Linacea, Euphorbiaceae, Convolvulaceae Rosaceae, Cucurbitaceae, Theaceae, Rubiaceae, Sterculiaceae or Citrus. It is particularly preferred that the plant is of the family Fabaceae, Solanaceae or Brassicaceae. If the plant is of the family Fabaceae, the plant is, preferably, of the genus *Glycine, Pisum, Arachis, Cicer, Vicia, Phaseolus, Lupinus, Medicago* or Lens. Preferred species of the family Fabaceae are *Medicago truncatula, Medicago sativa, Glycine max, Glycine soja, Pisum sativum, Archis hypogea, Cicer arietinum, Vicia faba, Phaseolus vulgaris, Phaseolus acutifolius, Lupinus albus, Lupinus luteus, Lupinus angustifolius* or *Lens culinaris*. More preferred are the species *Glycine max, Archis hypogea* and *Medicago sativa*. The most preferred species is *Glycine max*. Preferred genotypes of *G. max* are the genotypes used in the Examples.

When the plant is of the family Solanaceae, the preferred genus is *Solanum, Lycopersicon, Nicotiana* or *Capsicum*. Preferred species of the family Solanaceae are *S. tuberosum, L. esculentum* (also known as *Solanum lycopersicon*), *N. tabaccum* or *C. chinense*. More preferred is *S. tuberosum*.

When the plant is of the family Chenopodiaceae, the preferred genus is Beta or *Spinacia* Preferred species are *B. vulgaris* and *S. oleracea*.

When the plant is of the family Asteraceae, the preferred genus is *Helianthus* and the preferred species is *H. annuus*.

In one preferred embodiment the plant is of the family Brassicaceae. If the plant is of the family Brassicaceae, the plant is, preferably, of the genus *Brassica* or *Raphanus*. Preferred species of the genus of the genus *Brassica* are the species *B. napus, B. oleracea, B. juncea* or *B. rapa*. Most preferred is the species *B. napus*.

When the plant is of the family Malvaceae, the preferred genus is *Gossypium* or *Abelmoschus*. When the genus is *Gossypium*, the preferred species is *G. hirsutum* or *G. barbadense*. The most preferred species is *G. hirsutum*. A preferred species of the genus *Abelmoschus* is the species *A. esculentus*.

When the plant is of the family Linacea, the preferred genus is *Linum*. The preferred species is *L. usitatissimum*.

When the plant is of the family Euphorbiaceae, the preferred genus is *Manihot, Jatropha* or *Rhizinus* and the preferred species is *M. esculenta, J. curcas* or *R. communis*.

When the plant is of the family Convolvulaceae, the preferred genus is *Ipomea*. The preferred species is *I. batatas*.

Particularly preferred plant species are *Medicago truncatula, Medicago sativa, Glycine max, Glycine soja, Pisum sativum, Archis hypogea, Cicer arietinum, Lupinus albus, Lupinus luteus, Lupinus angustifolius, P. acutifolius* and *P vulgaris*. More preferred are the species *Glycine max, Archis hypogeal*, and *P. vulgaris* and *Medicago sativa*. The most preferred species is *Glycine max*.

The wounded transformable explant to be used in the method of the present invention shall comprise at least one cotyledon, and wounded tissue selected from wounded meristematic tissue of a primary or higher leaf node, wounded meristematic tissue of the cotyledonary node, and wounded epicotyl tissue. In a preferred embodiment, the wounded transformable explant further comprises a hypocotyl or a portion thereof.

In the context of the method of the present invention, the wounded transformable explant is, preferably, derived/obtained from a seedling.

Preferably, the seedling is a 3 to 20 days old seedling. More preferably, said seedling is a 5 to 12 days old seedling. Even more preferably, it is a 4 to 12 days old seeding, or a 6 to 10 days old seedling. Most preferably, said seedling is a 7 to 8 days old seedling. Preferably, the age of a seedling is calculated from the germination of the seedling.

It is particularly contemplated that the seedling has been grown under in vitro conditions, i.e. under sterile conditions. However, it is also contemplated that the seedling has been grown under non-sterile conditions.

In the context of the method of the present invention, the wounded transformable explant is, preferably, obtained from a seedling by wounding said seedling i) in the meristematic tissue of a primary or higher leaf node, ii) in the meristematic tissue of the cotyledonary node, or iii) in the epicotyl region. Preferably, the wounded tissue is the target tissue of the transformation, i.e. cells comprised by the target tissue are transformed with the polynucleotide comprising at least one plant expression cassette for a selectable marker gene.

Thus, in case meristematic tissue of the cotyledonary node is wounded, the target tissue is meristematic tissue of the cotyledonary node. In case meristematic tissue of a primary or higher leaf node is wounded, the target tissue is meristematic tissue of a primary or higher leaf node.

In case epicotyl tissue is wounded, the target tissue is epicotyl tissue, preferably the tissue at which the epicotyl tissue has been wounded.

The terms "meristematic cells" or "meristematic tissue" are known by the skilled person. The term, preferably, refers to undifferentiated plant cells or tissue which continually divides and forms cells.

Preferably, the wounded meristematic tissue of the primary or higher leaf node is wounded apical meristematic tissue. More preferably, the wounded meristematic tissue of the primary or higher leaf node is wounded axillary meristematic tissue. Thus, the target tissue is, preferably, axillary meristematic tissue of a primary or higher leaf node.

The term "epicotyl" as used herein, preferably, refers to the portion of a plant located between cotyledonary node and primary leaf node.

Many methods of wounding can be used. Preferred methods are cutting, abrading, piercing, poking, penetration with fine particles or pressurized fluids, plasma wounding, application of hyperbaric pressure, or sonication. Wounding can be performed using objects such as scalpels, scissors, needles, abrasive objects, particles, electric gene guns, or sound waves.

In the context of the method of the present invention, wounding is preferably achieved by cutting the seedling i) in the meristematic tissue of the cotyledonary node, ii) in the epicotyl region, or iii) in the meristematic tissue of a primary or higher leaf node (depending on the target tissue). More preferably, said wounding is achieved by decapitating said seedling at the meristematic tissue of the cotyledonary node, within the epicotyl region, or within the meristematic tissue of a primary or higher leaf node.

The portion of the plant below the cut is used as the transformable explant. Thus, the parts of the seedling that are located above the cut, are preferably removed.

Moreover, it is also particularly envisaged that the following parts are removed from the seedling in order to obtain the wounded transformable explant:
  i. the roots,
  ii. the roots and a portion of the hypocotyl,
  iii. in case the explant is prepared from a dicotyledonous plant (which are the most preferred plants), one cotyledon is, preferably, removed.

The term "hypocotyl" as used herein, preferably, refers to the part of the seedling between the cotyledon(s) and the root. The use of a hypocotyl or portion thereof is advantageous since the hypocotyl can be inserted in the growing medium in step c) of the method of the present invention. Thereby, the explant can be better kept in an upward position.

It is particularly preferred that at least two thirds of the hypocotyl, and, more preferably, at least one third, or even more preferably, one tenth of the hypocotyl (as comprised by the seedling) remain(s) attached to the wounded transformable explant. Even more preferably, 0.5 to 2 cm, or 0.5 to 1 cm of the hypocotyl remain(s) attached to the explant. It is further contemplated 0.1 to 2 cm of the hypocotyl remain(s) attached to the explant.

Accordingly, the portion of the hypocotyl comprised by the wounded transformable explant comprises, preferably, at least two thirds, at least one third, or at least one tenth of the hypocotyl as comprised by the seedling. Also preferably, said portion comprises 0.5 to 2 cm, 0.5 to 1 cm, or 0.1 to 2 cm of the hypocotyl as comprised by the seedling. Moreover, it is also envisaged that the portion of the hypocotyl is less than one third, less than one fifth, or in particular, less than one tenth of the hypocotyl as comprised by the seedling. Thus, the portion of the hypocotyl, preferably, has a length of at least 0.2, 0.4, or 0.5 cm. However, if the target tissue is wounded meristematic tissue of a primary or higher leaf node, the hypocotyl may be completely removed from the plant. In this case, the explant to be transformed does not comprise hypocotyl tissue.

Preferably, if the seedling is wounded at the meristematic tissue of the cotyledonary node (e.g. by cutting or decapitating), the meristematic tissue of the cotyledonary node, or a portion thereof, remains attached to the transformable explant.

Thus, in a preferred embodiment of the method of the present invention, the wounded transformable explant derived from a seedling comprises:
  i. a hypocotyl or a portion thereof,
  ii. at least one cotyledon,
  iii. wounded meristematic tissue of the cotyledonary node.

Preferably, if the seedling is wounded at the epicotyl (e.g. by cutting or decapitating, see above), a portion of the wounded epicotyl remains attached to the transformable explant. The epicotyl may be wounded at any position.

Thus, in another preferred embodiment the wounded transformable explant derived from a seedling comprises:
  i. a hypocotyl or a portion thereof,
  ii. at least one cotyledon, and
  iii. wounded epicotyl tissue.

Preferably, if the seedling is wounded at the meristematic tissue of a primary or higher leaf node, a portion of the wounded tissue is attached to the transformable explant.

Thus, in a preferred embodiment of the method of the present invention, the wounded transformable explant derived from a seedling comprises:
  i. the hypocotyl or a portion thereof,
  ii. at least one cotyledon,
  iii the epicotyl, and
  iv. wounded meristematic tissue of a primary or higher leaf node.

In step b) of the method of the present invention, cells comprised by the said explant shall be transformed with a polynucleotide comprising at least one plant expression cassette for a selectable marker gene.

The polynucleotide to be transformed shall comprise at least one plant expression cassette for a selectable marker gene.

The term "selectable marker gene" as used herein, refers to a gene that—in the presence of the corresponding selection compound (herein also referred to as the "selection compound for the selectable marker gene") in the growing medium—confers a growth advantage to a plant or plant cell transformed with a plant expression cassette for said selectable marker as compared to a plant or plant cell not been transformed with said plant expression cassette and which, thus, does not comprise the selectable marker gene. Preferably, the selectable marker gene and/or plant expression cassette for said marker gene is heterologous to the plant to be transformed, and thus is not naturally present in the plant to be transformed.

Preferably, the selectable marker gene is a negative selection marker gene. Negative selection marker genes confer a resistance and/or increased tolerance to a selection compound.

Preferred selection compounds are herbicides.

In the context of the method of the present invention, the selection compound, preferably, is capable of being transported from the growing medium to the cells which have been transformed with the polynucleotide comprising at least one plant expression cassette for the selectable marker gene (thus, the marker gene that corresponds to the selection compound), and/or to cells which are derived from said cell (by cell division). Thus, the selection compound preferably is capable of being transported from the growing medium to the transformed cells/tissue comprising said polynucleotide. Preferably, the transport is through the vascular bundles of the explant, in particular through the phloem or xylem. Particularly preferred selection compounds that are capable of being transported through the explant are imidazolinone herbicides (see below) and D-amino acids, in particular D-alanine and D-serine, or herbicides having similarity to amino acids, like phosphinothricin, or glyphosate. Accordingly, marker genes which may also be employed in the invention are for example, but not excluding others:

Phosphinothricin acetyltransferases (PAT; also named Bialaphoeresistance; bar; De Block et al. (1987) Plant Physiol 91:694-701; EP 0 333 033; U.S. Pat. No. 4,975,374)

5-enolpyruvylshikimate-3-phosphate synthase (EPSPS; U.S. Pat. No. 5,633,435) or glyphosate oxidoreductase gene (U.S. Pat. No. 5,463,175) conferring resistance to Glyphosate™ (N-(phosphonomethyl)glycine) (Shah of al. (1986) Science 233: 478)

Glyphosate™ degrading enzymes (Glyphosate™ oxidoreductase; gox),

Sulfonylurea- and imidazolinone-inactivating acetolactate synthases (for example mutated ALS variants with, for example, the S4 and/or Hra mutation Bromoxynil™ degrading nitrilases (bxn)

Kanamycin- or. G418-resistance genes (NPTII; NPTI) coding e.g., for neomycin phosphotransferases (Fraley et al. (1983) Proc Natl Acad Sci USA 80:4803), which expresses an enzyme conferring resistance to the antibiotic kanamycin and the related antibiotics neomycin, paromomycin, gentamicin, and G418, Dicamba degrading enzymes (O-demethylase, oxygenase, ferredoxin) (Behrens et al. 2007 Science 316:1185-1188; U.S. Pat. No. 7,022,896)

marker genes that confer resistance against the toxic effects imposed by D-amino acids like e.g., D-alanine and D-serine (WO03/060133). Especially preferred as marker genes in this contest are the daoI gene (EC: 1.4. 3.3: GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3. 1.18; GenBank Acc.-No.: J01603).

Alternative marker genes are positive selection markers, which confer a growth advantage to a transformed plant in comparison with a non-transformed one. Such selection markers are described e.g., in EP-A 0 601 092. Positive selection markers may include (but shall not be limited to) mannose-6-phosphate isomerase (in combination with mannose), UDPgalactose-4-epimerase (in combination with e.g., galactose), wherein mannose-6-phosphate isomerase in combination with mannose is especially preferred.

Marker genes conferring a growth advantage might be used in combination with marker genes providing resistance against a herbicide, D-amino acid or antibiotic.

Particularly preferred marker genes are as follows:

A particularly preferred selectable marker gene is the acetohydroxy acid synthase (AHAS) gene, in particular a mutated AHAS gene. The acetohydroxy acid synthase enzyme (also known as acetolactate synthase, or ALS) is a protein found in plants and microorganisms and which catalyzes the first step in the synthesis of the branched-chain amino acids (valine, leucine, and isoleucine). Preferably, it has enzymatic activity as set forth in the Enzyme Commission Code EC 2.2.1.6. The mutated AHAS protein, preferably, confers resistance to at least one imidazolinone herbicide. Imidazolinone herbicides are well known in the art, and, preferably, include imazapyr, imazaquin, imazethapyr, imazapic, imazamox and imazamethabenz. Preferably, the imidazolinone herbicide is imazaquin. More preferably, the imidazolinone herbicide is imazethapyr. Most preferably, the imidazolinone herbicide is imazapyr.

Preferred mutated AHAS genes are disclosed in WO2004/005516 or WO2008/124495 which herewith is incorporated by reference with respect to its entire disclosure content. Further preferred mutated AHAS genes are disclosed in WO2006/015376 or WO2007/054555 or US20100287641. The mutated AHAS enzyme preferably confers resistance to imidazolinone herbicides.

The polynucleotide sequence of a particular preferred mutated AHAS gene is shown in GenBank-Accession Number FW503642.1 GI:313050309. The resulting mutated AHAS polypeptide comprises, inter alia, a S653N mutation.

Further preferred selection marker genes are marker genes that confer resistance or increased tolerance to the toxic effects imposed by D-amino acids. Such preferred marker genes, preferably, encode for proteins which are capable of metabolizing D-amino acids. Preferred D-amino acids are D-alanine and D-serine. Particularly preferred marker genes encode for D-serine ammonialyases, D-amino acid oxidases and D-alanine transaminases. Preferred examples for such marker genes encoding for proteins which are capable of metabolizing D-amino acids are those which are as disclosed in WO03/060133, WO05/090584, WO07/107,516 and WO08/077,570 which are herewith incorporated by reference with respect to their entire disclosure content.

Several methods are known for the transformation of plant cells. Transformation of cells comprised by the target tissue is, preferably, achieved by *Agrobacterium*-mediated transformation, by naked DNA transformation such as electroporation and PEG-mediated transformation, or by particle bombardment.

It is particularly preferred that step b) is carried out by co-cultivating the explant with *Agrobacterium* comprising a T-DNA. Said T-DNA shall comprise the polynucleotide comprising the at least one plant expression cassette for a selectable marker gene as referred to in step b) of the method of the present invention. Preferably, the co-cultivation of the explant with *Agrobacterium* shall allow for transforming cells comprised by the wounded transformable explant so that a chimeric explant is obtained. How to co-cultivate an explant with *Agrobacterium* is well known in the art and, e.g., described in US2009/0049567. In the context of the studies carried out in the context of the present invention, both solid and liquid co-cultivation media were successfully used for transformation. For co-cultivation, the explants are, preferably, inoculated with an *Agrobacterium* culture resuspended in liquid co-cultivation medium for a few minutes to a few hours, typically about 10 minutes to 3 hours, preferably about 0.5 hours to 1 hour. The *Agrobacterium* are permitted to co-cultivate with the target tissue for several days, typically three to five days in the dark, preferably, in liquid co-cultivation medium or on plates with (solidified) co-cultivation medium. Preferred co-cultivation media are described in the Examples section. During the co-cultivation step, the *Agrobacterium* transfers its T-DNA into some cells of the target tissue. Preferably, the co-cultivation is carried out under in vitro conditions, i.e. under sterile conditions. Normally no selection compound is present during this step.

Preferably, if the explant comprises wounded meristematic tissue of the primary or a higher leaf node (see above), cells comprised by said wounded meristematic tissue are transformed (see e.g. also US2009/0049567). Thus, cells comprised by the wounded meristematic tissue are the target of the transformation. Accordingly, the co-cultivation, preferably, shall allow for transforming cells comprised by the wounded meristematic tissue of the primary or a higher leaf node. Thereby, chimeric explants are obtained, i.e. explants comprising cells that are transformed with the at least one plant expression cassette for a selectable marker gene, and cells that not transformed with the at least one plant expression cassette for a selectable marker gene.

Preferably, if the explant comprises wounded meristematic tissue of the cotyledonary node, cells comprised by said wounded meristematic tissue are transformed. Thus, cells comprised by the wounded meristematic tissue of the cotyledonary node are the target of the transformation.

Accordingly, the co-cultivation, preferably, shall allow for transforming cells comprised by the wounded meristematic tissue of the cotyledonary node. Thereby, chimeric explants are obtained.

Preferably, if the explant comprises wounded epicotyl tissue, cells comprised by said wounded epicotyl tissue are transformed (see, e.g., Wright et al (Plant Cell, Tissue and Organ Culture 8: 83 to 90 (1987)). Thus, cells comprised by the wounded epicotyl tissue are the target of the transformation. Thereby, chimeric explants are obtained.

The term "*Agrobacterium*" as used herein means all species of the *Agrobacterium* family (including *Agrobacterium tumefaciens* and *Agrobacterium rhizogenes*). The principles of plant transformation by means of *Agrobacterium*-mediated DNA transfer are well known in the art (Horsch R B et al. (1985) Science 225: 1229 pp).

*Agrobacterium* is a soil borne phytopathogen that integrates a piece of DNA (T-DNA) into the genome of a large number of dicotyledonous and few monocotyledonous plants (Chilton, et al., 1977 Cell 11: 263-271; Hoekema, et al., 1985 Nature 303: 179-180; Bevan, 1984 Nucleic Acids Res. 12: 8711-8721; Sheng and Citovsky, 1996 The Plant Cell, Vol. 8.1699-1710). Preferred *Agrobacterium* strains are *Agrobacterium tumefaciens* which typically causes crown gall in infected plants, and *Agrobacterium rhizogenes* which typically causes hairy root disease in infected host plants. However, the *Agrobacterium* strains as used in the context of the present invention, preferably, shall lack the ability of causing crown gall disease and hairy root disease, respectively (which can be achieved by using disarmed *Agrobacterium* strains, see below).

The use of *Agrobacterium*, particularly, of *Agrobacterium tumefaciens* (but also of *Agrobacterium rhizogenes*) for plant transformation is known as such (for a review see Gelvin, 2003 Microbiol Mol Biol Rev. 67(1):16-37). For *Agrobacterium*-mediated plant transformation, the gene of interest is placed between the left and right border repeats of *Agrobacterium* T-DNA (transfer DNA). Afterwards, the T-DNA region containing the gene of interest is stably integrated into the plant genome by using an appropriate plant transformation protocol.

Various strains of *Agrobacterium* having different chromosomal backgrounds and Ti-plasmid content can be used for transformation. However, it is preferred that the *Agrobacterium* strain contains a disarmed Ti-plasmid or a disarmed Ri-plasmid. A disarmed Ti-plasmid is understood as a Ti-plasmid lacking its crown gall disease mediating properties but otherwise providing the functions for plant infection. A disarmed Ri-plasmid is understood as a Ri-plasmid lacking its hairy-root disease mediating properties but otherwise providing the functions for plant infection. *Agrobacterium* strains to be used for transforming plants cells are selected from LBA4404, GV2260, GV3600, EHA101, EHA105, AGL-1, LBA9402, GV3101, COR341, COR356, UIA143, pCH32, BIBAC2, C58C1, pMP90 and AGT121. In a preferred embodiment the *Agrobacterium* strain is selected from the group consisting of C58C1, EHA101, pMP90, SHA017, and LBA4404. In another preferred embodiment the *Agrobacterium* strain is a disarmed variant of K599 (NCPPB 2659) which, preferably, carries a disarmed variant of pRi2659 as disclosed in WO03/017752.

Preferably, the *Agrobacterium* to be used in the context of the method of the present invention, include a DNA construct (e.g., a binary vector) comprising a T-DNA which comprises an expression cassette for a selectable marker gene. Preferably, said T-DNA comprises at least one expression cassette for an agronomically valuable trait. As a result of the *Agrobacterium*-mediated transfer, said T-DNA will normally be present, i.e. stably integrated, in the genome of the transformed cells.

In order to allow for transformation, the *Agrobacteria* are prepared by known methods. The T-DNA comprising *Agrobacterium* strain may, for example, be grown in liquid YEP medium supplemented with the appropriate antibiotic. For co-cultivation, the bacteria are preferably resuspended in liquid co-cultivation medium. The concentration of *Agrobacterium* used for co-cultivation may be varied. Thus, generally a range of *Agrobacterium* concentrations from $OD_{600}$ 0.1 to 3.0 and a range of co-cultivation periods from a few hours to 7 days can be used. It is particularly preferred that the *Agrobacterium* concentration ranges from $OD_{600}$ 1.0 to 2.0. Another, also preferred method for the transformation of cells is particle bombardment The term "particle bombardment" as used herein, preferably, refers to the process of accelerating particles coated with the gene of interest towards a target biological sample (particularly cells, and plant tissue) in order to effectively wound the cell membrane of a cell in the target biological sample and/or entry of the particles into the target biological sample. Methods for particle bombardment (frequently also referred to as "biolistic bombardment") are known in the art, se, e.g., U.S. Pat. No. 5,584,807), and are commercially available (e.g., the helium gas-driven microprojectile accelerator (PDS-1000/He) (BioRad).

In a preferred embodiment, the method further comprises the step b1) of transferring the explant of step a) (in particular, a co-cultivated explant) to a shoot induction medium and cultivating said explant on said shoot induction medium. Preferably, the explant is transferred to said medium, preferably, by laying the explant on the shoot induction medium, preferably, in a horizontal position. It is also envisaged that the explant is submerged in said medium (preferably, also in horizontal position). By carrying out step b1), an explant is generated comprising shoot tissue comprising cells comprising the at least one plant expression cassette for a selectable marker gene. Said shoot tissue is herein also referred to as "de novo formed shoot tissue". Preferably, said shoot tissue is derived from the tissue which is the target of transformation.

Preferably, the shoot induction medium comprises at least one plant growth factor allowing for the induction of shoots, in particular a cytokinin. Preferably, said at least one plant growth factor is comprised by the said shoot induction medium in a concentration suitable to induce de novo shoot induction from the target tissue. Preferably, the shoot induction medium comprises a selection compound for the selectable marker gene comprised by the at least one plant expression cassette.

The term "plant growth factor" as used herein, preferably, encompasses naturally occurring or synthetic (not naturally occurring) compounds that can regulate plant growth and development. Preferred plants growth factors are cytokinins or auxin.

A preferred auxin is selected from the group consisting of indoleacetic acid (IAA), indole-3-butyric acid (IBA), naphthylacetic acid (NAA), and 2,4-dichlorphenoxyacetic acid (2,4-D). A particularly preferred auxin is IAA (see Examples for preferred concentrations).

Preferred cytokinins are kinetin, zeatin, 6-isopentenyladenine (IPA) and 6-benzyladenine/6-benzylaminopurine (BAP).

The shoot induction medium, preferably, comprises cytokinins, in particular kinetin and/or BAP.

The shoot induction medium may further contain an antibiotic in order to stop or retard growth of the remaining *Agrobacterium* cells. Preferably, said antibiotic is not the selection compound for the selectable marker gene that shall be transformed into the plant. Preferred antibiotics are carbenicillin or Timentin® which is a mixture of ticarcillin disodium and clavulanate potassium. Preferably, the antibiotic is contained by the medium in an amount suitable to stop or retard growth of *Agrobacterium* cells. Alternatively, the explants may be washed with a solution contain said antibiotic after co-cultivation.

The shoot induction medium, preferably, further comprises a selection compound (for the selectable marker gene used for transformation) in an amount that is sufficient to allow for the selection of transgenic cells. An explanation of the term "in an amount that is sufficient to allow for the selection of transgenic cells" is given herein below in the context of step c) of the method of the present invention. Preferred amounts of the selection compounds as given in the context of step c) also apply to the shoot induction medium.

The explants are, preferably, incubated on said shoot induction medium until shoots have been developed. Formation of transgenic shoot primordia becomes visible around 1 week on shoot induction medium and, on average, explants are cultured in a shoot induction medium for about 3 to 6 weeks to allow most explants to form new shoots. Therefore, the explants may be cultivated for up to 5 weeks on shoot induction medium. However, the cultivation of the explant on shoot induction medium may be significantly shorter than 5 weeks since it has been surprisingly shown in the studies carried out in the context of the present invention, that the cultivation time on shoot induction medium can be reduced when carrying out the method of the present invention. This surprising effect results in an overall reduction of time needed for obtaining fully regenerated plants. Accordingly, in step b1) of the method of the present invention, the explants are preferably, cultivated on shoot induction medium for 1 to 4 weeks, more preferably, for 1 to 3 weeks, even more preferably, for 2 to 3 weeks before transferring the explants to a growing medium as described herein below.

In step c) of the method of the present invention the explant shall be transferred to a growing medium. The growing medium shall allow for promoting elongation of transgenic shoots if step b1) has been carried out. The growing medium shall allow for de novo formation of transgenic shoots and for elongation of transgenic shoots if step b1) has not been carried out. The growing medium can be any medium which allows for the elongation of transgenic shoots and for the growth of a plant (see below). In the context of the method of the present invention, the growing medium, preferably, comprises at least one selection compound for said selectable marker gene. Preferably, said at least one selection compound is comprised by the growing medium in an amount that is sufficient to allow for the selection of transgenic cells, i.e. of cells that comprise the polynucleotide comprising the plant expression cassette as referred to above. Preferably, the explant obtained by carrying out step b1) i.e. the explant which was incubated on shoot induction medium and which comprises de novo formed shoot tissue is transferred to the growing medium. However, it is also envisaged that step c) of the method of the present invention is carried out immediately after step b) (and, thus, without carrying out step b1). Particularly, it is envisaged to transfer the explant that has been co-cultivated (in step b)) with *Agrobacterium* comprising a T-DNA as described above directly to the growing medium. In this case the growing medium shall allow for the formation and elongation of transgenic shoots. If step b1) has been carried out (and, thus, if the explant has been cultivated on shoot induction medium), the de novo formed shoot comprised by the explant, preferably, shall be allowed to elongate after transferring the explant to the growing medium. How to achieve the formation of and elongation of transgenic shoots is well known in the art.

Preferably, the explant is placed vertically (and, thus, in an upward position) in the growing medium with the target tissue up. More preferably, the explant is placed vertically in the growing medium with the target tissue up so that the target tissue comprised by the explant is not in direct contact with the surface of the growing medium. This is, preferably, achieved by inserting the hypocotyl or a portion thereof comprised by the explant into the growing medium. Preferably, the at least one cotyledon is not inserted into the growing medium. Thus, it shall, preferably, remain above the surface of the growing medium.

After inserting said hypocotyl or the portion thereof into said growing medium, said explant is, preferably, in an upward position (so that the target tissue comprised by the explant is not in direct contact with the surface of the growing medium). This also applies if the further step b1) has been carried out. In this case, the de novo formed shoot tissue comprised by the explant shall not be in direct contact with the surface of the growing medium after the transfer of the explant to said growing medium.

Of course, not the entire hypocotyl has to be inserted into the growing medium. It is sufficient to insert a portion of the hypocotyl into said growing medium which is sufficient to keep the explant in an upward position. Which portion allows for keeping the explant in an upward position can be determined by the person skilled in the art without further ado.

If the explant does not comprise a cotyledon (which may be the case if the cotyledon falls off when trying to insert it in the hole) a portion of the epicotyl is, preferably, inserted into the growing medium. In this case, the explant shall be also placed vertically in the growing medium so that the target tissue is not in direct contact with the surface of the growing medium.

However, it is particularly envisaged that the epicotyl remains above the surface of the growing medium after transfer to the growing medium.

The growing medium can be any medium which allows for the growth of plants. Preferably, the growing medium is a solid medium.

Preferably, the growing medium (herein also referred to as "growth medium") is selected from the group consisting soil, humus, and a hydroponic medium. The most preferred growing media are hydroponic media. Preferably, the explant is cultivated under ex vitro conditions, and, thus, under non-sterile conditions, after transferring said explant to said growing medium.

Moreover, it is also envisaged that the growing medium is a plant tissue culture medium. In this case, step c) is carried out under in vitro conditions, i.e. under sterile conditions. Preferably, the plant tissue culture medium is selected from the group consisting of Gamborg B5 medium, Murashige & Skoog medium, Linsmaier & Skoog medium, and Murashige & Miller medium. Of these, the Gamborg B5 and the Murashige & Skoog media are particularly preferred.

The use of hydroponics for the growth of plants is known as such (for a review see Hydroponics: A Practical Guide for the Soilless Grower, J. Benton Jones, published CRC Press, 2004). Hydroponics is a technology of growing plants in nutrient solutions without soil. The two main types of hydroponics are liquid hydroponic mediums and substrate hydroponic mediums. In the context of the method of the present invention the hydroponic medium is a substrate hydroponic medium and, thus, a soil-less cultivation medium that comprises a hydroponic compound and a nutrient medium.

Preferably, the hydroponic compound comprised by the hydroponic medium is inorganic. More preferably, the hydroponic compound is a mineral wool. Most preferably, the hydroponic compound is acidic phenol-formaldehyde-, urea formaldehyde- or cellulose-based foams. Such foams, preferably, have an open cell structure mimicking the plant cellular structure. Preferred foams are available as Oasis® root medium from Smithers-Oasis Co. also called Oasis® wedges, (Kent, Ohio, USA) or are available as cellular foam rooting sponges from Grow-Tech (Lisbon Falls, Me., USA). E.g., preferred acidic phenol formaldehyde based foams (also know as phenolic foams) are described in U.S. Pat. No. 2,753,277.

Mineral wool hydroponic compounds for plant growth are known in the art and, preferably, comprised of coherent matrix of mineral fibers made from natural or synthetic minerals or metal oxides. Preferably, the mineral wool is selected from the group consisting of glass wool, rock wool and slag wool. Also contemplated are mixtures of the aforementioned mineral wools. The most preferred mineral wool in the context of the present invention is rock wool (see also WO01/87070). Rock wool, frequently also referred to as stone wool, is a mineral wool manufactured from volcanic rock. It is comprised of pores (about 95%) and solids in the form of rock fibres (5%). Preferably, the rock wool is manufactured from basalt and limestone. For manufacturing rock-wool, these raw materials are, e.g., heated in an oven at about 1500° C., when they melt into lava. The lava may then poured onto a number of discs spinning at a high speed. The centrifugal force throws drops of lava from the discs, which are then transformed into threads. The threads are compressed to form a solid mass, which then may be sawn into slabs and blocks.

It is to be understood that the hydroponic medium can be provided in many shapes and sizes, e.g., mini cubes, cubes, blocks, mats and slabs (see also Examples).

Of course, the growing medium shall also comprise nutrients. The medium, preferably, comprises essential elements needed by the plant for growth and development such as nitrogen, phosphorous, and potassium. Preferably, the growing medium also comprises a plant growth regulator, in particular an auxin such as IAA.

In the context of the method of the present invention, the growing medium as referred to above shall comprise at least one selection compound for the selectable marker gene comprised by the expression cassette described above. The selection compound, preferably, is already present in the growing medium when explant is transferred to the growing medium. However, it is also contemplated that the selection compound is added to the growing medium after the transfer. If the selection compound is added after the transfer, the compound is, preferably, added immediately, one day, two days, three days or four days after the transfer. Preferably, the selection compound is added by watering the explants with a solution containing the selection compound, in particular once or twice a week.

Preferably, the growing medium also comprises a plant growth factor, in particular IAA. The plant growth factor, preferably, is already present in the growing medium when explant is transferred to the growing medium. However, it is also contemplated that the selection compound is added to the growing medium after the transfer (see above). The plant growth factor, preferably, allows for root induction.

As set forth above, the selection compound shall be comprised by the growing medium in an amount that is sufficient to allow for the selection of transgenic cells. The amount of the selection compound in the medium that is sufficient may depend on the plant to be transformed as well as on the selection compound itself. Sufficient amounts of the selection compound, however, can be determined by the person skilled in the art without further ado. E.g. sufficient amounts can be determined by comparison experiments in which various amounts of the selection compounds are tested. Usually, an amount of the selection compound may be regarded as sufficient, if the growth of cells which have not been transformed with a plant expression cassette for the corresponding selectable marker is inhibited, whereas cells which have been successfully transformed with said plant expression cassette are capable of growing (and, thus, cell division takes place). Preferred amounts of specific selection compounds that are considered to be sufficient to allow for the selection of transgenic cells are given herein below.

If the selectable marker gene encodes for AHAS or a mutated AHAS, the growing medium comprises preferably, at least one Imidazolinone herbicide (i.e the corresponding selection compound), in particular Imazapyr, in an amount of, preferably, 0.5 µM to 25 µM, more preferably, of 1 µM to 10 µM, and, even more preferably of 1 µM to 5 µM, most preferably of 1 µM to 3 µM. It is also preferred to water the explants with a solution containing the aforementioned amounts of the selection compound. Further preferred amounts of Imazapyr are given in the Examples.

If the selectable marker gene confers resistance or increased tolerance against the toxic effects imposed by D-amino acids (in particular if the marker gene encodes for a D-serine ammonialyase) the growing medium, preferably, comprises at least one D-amino acid, in particular D-serine, in an amount of 0.05 mM to 100 mM, preferably 0.1 mM to 50 mM, and more preferably 5 mM to 7.5 mM. It is also preferred to water the explants with a solution containing the aforementioned amounts of the selection compound.

Preferred concentrations of other selective compounds are for example:

With the phosphinothricin resistance gene (bar) as the selective marker, phosphinothricin may be included in the medium at a concentration of from about 1 to 75 mg/l. Typical concentrations for selection are from about 1 to about 15 mg/l. The preferred concentrations for selection are about 3 to 5 mg/l.

With the kanamycin resistance gene (neomycin phosphotransferase, NPTII) as the selective marker, kanamycin at a concentration of from about 3 to 200 mg/l may be included in the medium. Typical concentrations for selection are 5 to 50 mg/l.

It is known that plants generally may be selected by contacting the selection compound by spraying the plants/explants with a solution containing the selecting agent or by adding the selection compound onto the leaves of the plant/explant. However, in the context of the present invention, the selection compound shall be present in the growing medium. Thus, it is taken up by the non-transgenic parts of the explant and is translocated to epicotyls and above, rather than being contacted with the plant/explant by spraying the plants/explants with a solution containing the selecting agent or by adding the selection compound onto the leaves of the plant/explant.

In a further step d) of the method of the present invention said explant shall be allowed to form a shoot and the shoot shall be allowed to elongate. If step b1) has been carried out, the formed shoot (or formed shoot primordium) shall be allowed to elongate. The formed/elongated shoot, preferably, comprises plant cells comprising said least one plant expression cassette for said selectable marker gene.

Step d) may be carried out under in vitro or ex vitro conditions. Preferably, step d) is carried out under in vitro conditions, if the growing medium is a plant tissue culture medium. If the growing medium is a hydroponic medium, soil or humus, step d) is preferably, carried out under ex vitro conditions and, thus, under non-sterile conditions.

The elongation of shoots on hydroponic medium is advantageous since it takes only 2 weeks to get elongated shoots as compared to 6-8 weeks in a plant tissue culture medium. Thereby, the time needed for producing transgenic plants can be significantly reduced.

The method of the present invention, preferably, comprises the further step e) of regenerating a transgenic plant from said shoot formed and/or elongated in step d), and thus, from the plantlet derived from step d). The regenerated plants, preferably, comprise inserted into their genome the polynucleotide comprising said at least one plant expression cassette for said selectable marker gene.

In a preferred embodiment, step e) comprises the steps of
e1) separating the elongated shoot obtained in step d) from the explant,
e2) transferring the separated elongated shoot to a growing medium, and
e3) regenerating a transgenic plant from said elongated shoot.

In step e1) only elongated shoots are, preferably, separated. Whether a shoot can be considered as elongated can be determined by the skilled person without further ado. Preferably, the elongated shoots that are separated are shoots with full trifoliate leaf formation. If a soybean explant has been transformed, shoots with elongated stems having a length of, preferably, at least 2 cm, or more preferably, of at least 3 cm, or, even more preferably, of at least 5 cm are separated.

The separation of the elongated shoot from the explant can be carried out by any method deemed appropriate. Preferably, the separation is done by cutting the elongated shoot from the explant using a pair of scissors.

The separated elongated shoots shall be transferred to a growing medium. The term "growing medium" has been described above. Preferably, the growing medium is a hydroponic medium. The growing medium used for the regeneration of the plant may or may not comprise the selection compound for the selectable marker gene. Preferably, it comprises the selection compound. The separated shoot(s) is/are transferred to the growing medium to induce root formation. Root formation, preferably, takes 1 to 2 weeks. The plants may be grown to maturity on the growing medium. However, it is preferred to transfer the plantlets having developed roots to soil and to grow them to full maturity on soil (e.g. if they have been transferred to a hydroponic medium in step e2). After the transfer to soil, the rooted shoots may be kept in the growth chamber for 1 to 3 weeks before they are transferred to the greenhouse.

In a further step e4), the regenerated plants are allowed to develop seeds. Preferably, the seeds are collected in a further step e5). Preferably, the cells comprised by the seeds comprise the polynucleotide comprising the at least one plant expression cassette for a selectable marker gene (see, e.g. step a) of the method of the present invention, and are, thus, transformed with said plant expression cassette. Preferably, the cells are stably transformed with said plant expression cassette. The term "stably transformed" as used herein, preferably, means that the polynucleotide comprising the at least one plant expression cassette for a selectable marker gene is integrated into genome of the cells.

In an even further preferred embodiment of the method of the present invention, the plant in step e) is regenerated without separating the elongated shoot from said explant. The plants may be grown to maturity on the growing medium. However, it is preferred to transfer the plantlets having developed roots to soil and to grow them to full maturity on soil. Preferably, the plant is allowed to develop flowers. More preferably, the plant is allowed to develop seeds. In a further step, the developed seeds may be collected. Preferably, the cells comprised by the seeds comprise the polynucleotide comprising the at least one plant expression cassette for a selectable marker gene (see, e.g. step a) of the method of the present invention, and are, thus, transformed with said plant expression cassette. Preferably, the cells are stably transformed with said plant expression cassette.

By carrying out step e) without separating the elongated shoot from the explant, a plant is regenerated comprising non-transgenic epicotyl and/or hypocotyl tissue, i.e. tissue that is not transformed with the polynucleotide comprising the at least one plant expression cassette for a selectable marker, and transgenic tissues/organs such as the stem, leaves, flowers and/or seeds which are derived from the transformed cells of the target tissue of the transformation.

Said transgenic tissue/organs comprise the polynucleotide comprising at least one plant expression cassette for a selectable marker.

Accordingly, the present invention relates to a plant obtained or obtainable by the method of the present invention. In one embodiment, said plant obtained or obtainable by the method of the present invention is a composite plant. A composite plant, is a plant which comprises non-transgenic parts, in particular epicotyl and/or hypocotyl tissue and transgenic parts which are derived from the transformed plant cell. Said plant may be created by inducing transgenic shoots on a wildtype epicotyl and/or hypocotyl tissue under selective conditions and then transferring the wildtype epicotyl and/or hypocotyl tissue comprising transgenic shoots to a rooting step under non-selective conditions. "Non transgenic" in the context of the plant obtained or obtainable by the method of the present invention means that the tissues or parts of the plant referred to above do not comprise, and, thus, have not been transformed with the polynucleotide comprising at least one expression cassette for a selectable marker.

Figure 3:
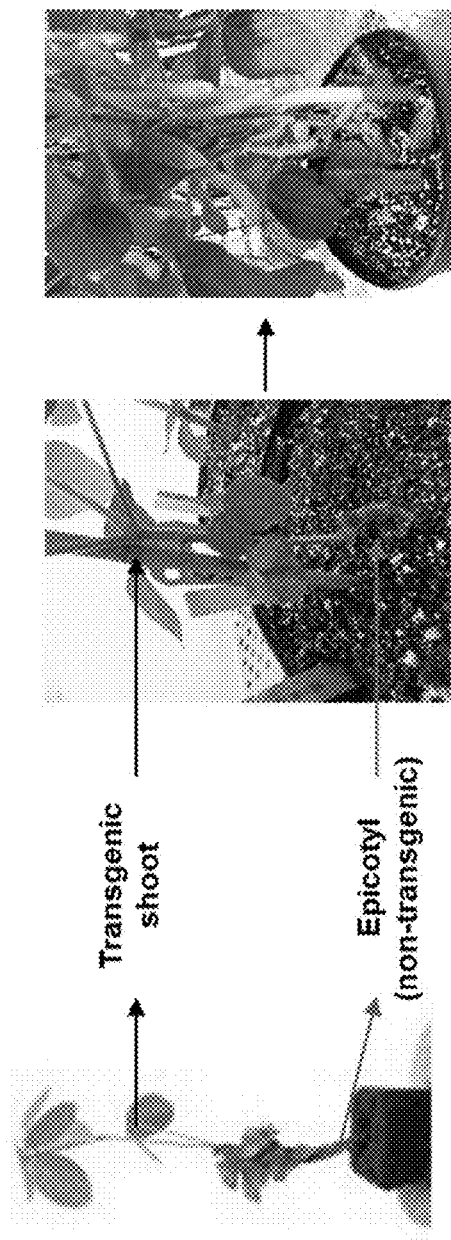
Figure 3:
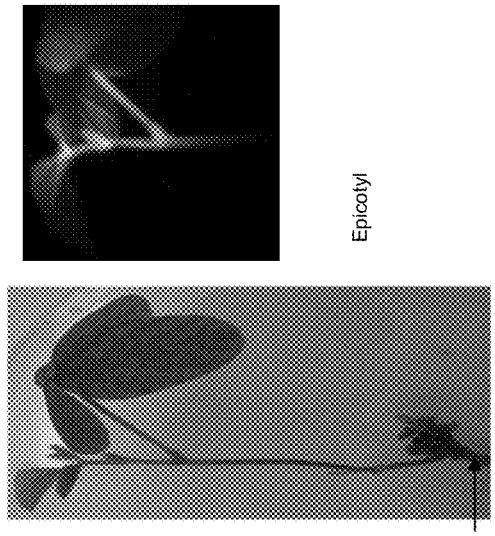

Preferably, said plant has developed flowers. More preferably, said plant has developed seeds. Most preferably, the seeds developed by the plant comprise the transformed polynucleotide comprising at least one plant expression cassette for a selectable marker. Thus, the transformed polynucleotide will be transmitted to the following generation. FIG. 3 shows a composite plant.

The present invention is advantageous for the following reasons:

Usually, transgenic plants are obtained by transforming a plant tissue susceptible to *Agrobacterium*-mediated transformation with a suitable *Agrobacterium* strain. After co-cultivation, the explant is incubated on shoot induction medium and transgenic shoots are selected by using a selectable marker gene. After shoot elongation, shoots are separated from the explants and root growth is induced on a root induction medium. Usually all these steps are carried out under in vitro conditions, i.e. under sterile conditions. Thus, many steps are carried out under sterile conditions. This increases the risk of fungal or bacterial contamination. Moreover, the aforementioned protocol is very time-consuming. E.g., when transforming soybean as described above, the transformation takes as many as 100 days or even more.

However, when applying the method of the present invention, the timeline for soybean transformation can be shortened and rooted transgenic soybean plants may be obtained within 50-60 days. In particular, the timeline can be shortened when incubating the explant only for a short time on shoot induction medium, and/or when the plants are grown to maturity without separating the elongated shoots from the explants. This has been shown for various soybean varieties such as 93061, Williams82, Stoddard and Jake as well as for *A. tumefaciens* and *A. rhizogenes*.

In accordance with the method of the present invention, the explants are placed vertically on the growing medium, e.g soil, humus, or a hydroponic medium, with their residual hypocotyl part inserted into the growing medium, e.g. a hydroponic medium, like Oasis™ wedges. Nevertheless, the selection has been shown to be effective although the transformed plant cells comprised by the explant are not in direct contact with the surface of the growing medium comprising the selection compound. Only the non-transformed hypocotyl/cotyledonary tissue is in direct contact with the growing medium and, thus, with the selection compound. Thus, the results of the studies carried out in accordance with the present invention are surprising.

Moreover, the use of hydroponic media is advantageous since it significantly reduces the time needed for shoot elongation as compared to other systems, e.g. in a plant tissue culture medium. Thereby, the overall time needed for producing transgenic plants can be significantly reduced.

Moreover, when applying the method of the present invention, the number of steps carried out under in vitro condition can be reduced resulting in a reduced risk of contamination.

Moreover, when carrying out step e) without separating the elongated shoot from the explant the number of steps required for obtaining a transgenic plant and/or transgenic seeds can be reduced.

The definitions and explanation given herein above in the context of the first method of the present invention, apply mutatis mutandis to the method of the present invention described herein below (except if stated otherwise).

Moreover, the present invention relates to a method for producing a transgenic plant, comprising the steps of
(i) providing a wounded transformable explant, comprising at least one cotyledon, and wounded meristematic tissue of a primary or higher leaf node (in particular wounded axillary meristematic tissue of a primary or higher leaf node),
(ii) transforming cells comprised by the said explant with a polynucleotide comprising at least one plant expression cassette for a selectable marker gene,
(iii) transferring said explant to a shoot induction medium and cultivating said explant on said shoot induction medium comprising at least one selection compound for said selectable marker gene, thereby allowing formation of at least one de novo formed shoot comprising plant cells comprising said least one plant expression cassette for said selectable marker gene,
(iv) separating the meristem region of said primary or higher leaf node comprising said at least one de novo formed shoot and transferring said meristem region a hydroponic medium, said hydroponic medium comprising at least one selection compound for said selectable marker gene, and allowing said at least one de novo formed shoot to elongate, and
(v) regenerating a transgenic plant from said so derived plantlet.

Preferably, steps (i) and (ii) of the aforementioned method correspond to steps (a) and (b) of the first method described in this specification. Moreover, the wounded transformable explant may further comprise a hypocotyl or a portion thereof as described elsewhere herein. However, it is also preferred that the wounded transformable explant does not comprise hypocotyl tissue. Preferably, the explant is obtained by removing the roots and the hypocotyl or part thereof from the seedling. Also one cotyledon may be removed. Of course, the wounded transformable explant comprises the epicotyl.

Preferably, steps (i) and (ii) are carried out under in vitro conditions.

Preferably, step (iii) of the aforementioned method corresponds to step (b1) of the first method described in this specification. By carrying out step (iii), the explants, in particular, the co-cultivated explants, are preferably allowed to form shoots comprising plant cells comprising said least one plant expression cassette for said selectable marker gene (de novo shoot formation). Preferably, the shoot induction medium comprises at least one plant growth factor allowing for the induction of shoots. Preferred plant growth factors allowing for the induction of shoots, i.e. for de novo formation of shoots are described elsewhere herein. Preferably, step (iii) is also carried out under in vitro conditions.

The explant is, preferably, incubated on said shoot induction medium until de novo formed shoots have been developed. Therefore, the explant may be cultivated for up to 5 weeks on shoot induction medium. In accordance with the aforementioned method, the explant is, preferably, cultivated on shoot induction medium for 3 to 5 weeks, more preferably, for 3 to 4 weeks, even more preferably, for 3 weeks before transferring the explants to a growing medium as described herein below. It is also contemplated that the explants are cultivated on shoot induction medium.

After cultivation on shoot induction medium, the meristem region of the primary or higher leaf node comprises a cluster of newly formed leaf or shoot structures. Thus, the shoots from a cluster of shoots (a shoot aggregate). Preferably, at least one of the de novo formed shoots (in particular one) comprises plant cells comprising said least one plant expression cassette for said selectable marker gene.

Some of the shoots comprised by the cluster may be non-transgenic. It is, however, preferred that at least one de novo formed shoot comprises plant cells comprising said least one plant expression cassette for said selectable marker gene.

In step iv) the meristem region (and, thus, the meristem) of primary or higher leaf node comprising the at least one de novo formed shoot (comprising plant cells comprising said least one plant expression cassette for said selectable marker gene) is isolated, and, thus separated from the explants. Preferably, the meristem region is separated from the explant, by separating it from the epicotyl. The separation from the explant can be carried out by any method deemed appropriate. Preferably, the separation is done by cutting the meristem region from the explant using a pair of scissors. The separated meristem region, preferably, comprises a portion of the epicotyl.

The separated meristem region is then transferred to a hydroponic medium, preferably by inserting a portion of it into the hydroponic medium. (for preferred hydroponic media, see elsewhere herein, in particular step c) of the first method described in this specification). If the separated meristem region comprises a portion of the epicotyl, said portion of the epicotyl is preferably inserted into the hydroponic medium. Preferably, said meristem region is inserted into the hydroponic medium in an upward position.

Said hydroponic medium, preferably, comprises at least one selection compound for said selectable marker gene (for details, see also step c) of the first method). Moreover, after the transfer, the at least one shoot comprising plant cells comprising said least one plant expression cassette for said selectable marker gene shall be allowed to elongate. Moreover, the at least one shoot shall be allowed to form roots. This may be achieved by adding suitable plant growth factors. Thereby, plantlets are obtained which are transformed with the polynucleotide comprising the at least one plant expression cassette for a selectable marker gene.

In contrast to steps (i) to (iii), step (iv) shall be, preferably, carried out under non-sterile, and thus, under ex vitro conditions.

In a further step (v), plants are regenerated from the plantlets derived from step (iv). The regenerated plants, preferably, comprise inserted into their genome the polynucleotide comprising said at least one plant expression cassette for said selectable marker gene. Preferably, the regenerated plants are allowed to develop seeds. Preferably, said seeds are collected. Preferably, the cells comprised by the seeds comprise the polynucleotide comprising the at least one plant expression cassette for a selectable marker gene (see, e.g. step a) of the method of the present invention, and are, thus, transformed with said plant expression cassette. Preferably, the cells are stably transformed with said plant expression cassette. The term "stably transformed" as used herein, preferably, means that the polynucleotide comprising the at least one plant expression cassette for a selectable marker gene is integrated into genome of the cells.

Advantageously, it has been shown in the context of studies carried out for the present invention that the promotion of shoot elongation and root formation on a hydroponic medium, preferably, ex vitro has greatly reduced the timeline in generating transgenic plants as compared to the promotion of shoot elongation and/or root formation on other systems. For example, the time needed for shoot elongation could be reduced from 6 to 10 weeks to approximately 28 days.

All references cited in this specification are herewith incorporated by reference with respect to their entire disclosure content and the disclosure content specifically mentioned in this specification.

In the following, preferred embodiments of the present invention are disclosed. The definitions and explanations given herein above apply mutatis mutandis.

EMBODIMENTS

1. A method for producing a transgenic plant, comprising the steps of
   a) providing a wounded transformable explant, comprising a hypocotyl or a portion thereof, at least one cotyledon, and wounded tissue selected from
      i. wounded meristematic tissue of a primary or higher leaf node,
      ii. wounded meristematic tissue of the cotyledonary node, and
      iii. wounded epicotyl tissue
   b) transforming cells comprised by the said explant with a polynucleotide comprising at least one plant expression cassette for a selectable marker gene,
   c) transferring said explant to a growing medium by inserting the hypocotyl, or portion thereof, of said explant into said growing medium comprising at least one selection compound for said selectable marker gene,
   d) allowing said explant to form a shoot and/or allowing the shoot to elongate, said shoot comprising plant cells comprising said polynucleotide comprising said least one plant expression cassette for said selectable marker gene, and
   e) regenerating a transgenic plant from said shoot.
2. The method of embodiment 1, wherein step b) is carried out by co-cultivating said explant with *Agrobacterium* comprising a T-DNA, said T-DNA comprising the polynucleotide comprising at least one plant expression cassette for a selectable marker gene.
3. The method of embodiments 1, wherein the explant in step a) is derived from a 6 to 10 day old seedling.
4. The method of embodiments 2 and 3, wherein the co-cultivation allows for transforming cells comprised by the wounded meristematic tissue so that a chimeric explant is obtained.
5. The method of any one of embodiments 1 to 4, wherein the method comprises a further step b1) of transferring said explant to a shoot induction medium and cultivating said explant on said shoot induction medium.
6. The method of any one of embodiments 1 to 4, wherein step c) is carried out immediately after step b).
7. The method of any one of embodiments 1 to 6, wherein the explant is cultivated under ex vitro conditions after transferring said explant to a growing medium.
8. The method of any one of embodiments 1 to 7, wherein step e) comprises the steps of e1) separating the elongated shoot obtained in step d) from the explant,
e2) transferring the separated elongated shoot to a growing medium, and
e3) regenerating a transgenic plant from said elongated shoot.
9. The method of any one of embodiments 1 to 7, wherein the transgenic plant in step e) is regenerated without separating the elongated shoot from said explant.
10. The method of any one of embodiments 1 to 9, wherein the growing medium is step c) is a hydroponic medium.
11. The method of embodiment 10, wherein the hydroponic medium is a formaldehyde or cellulose based foam.
12. The method of any one of embodiments 1 to 11, wherein the selectable marker gene is a mutated AHAS gene (acetohydroxyacid synthase gene) or a marker gene that confers resistance or increased tolerance to against the toxic effects imposed by D-amino acids, in particular, a marker gene that encodes for a D-serine ammonialyase, a D-amino acid oxidase, or a D-alanine transaminase.
13. The method of embodiment 12, wherein the selectable marker gene is a mutated AHAS gene, and wherein the selection compound is an imidazolinone herbicide, in particular Imazapyr.
14. The method of any one of embodiments 1 to 13, wherein the plant is a dicotyledonous plant.
15. The method of any one of embodiments 1 to 14, wherein the genus of the plant is selected from the group consisting of Glycine, *Medicago* and *Phaseolus*.
16. The method of embodiment 15, wherein the plant is *Glycine max*.
17. A plant obtainable by the method of embodiment 9.
18. The plant of embodiment 17, wherein the plant has developed flowers.
19. The plant of embodiments 17 and 18, wherein the plant has developed seeds.

The Figures show:

FIG. 1A: Preparation of explants: Explants are prepared by removing most of the hypocotyl, one cotyledon and all preformed leaves (including apical meristem) from 7 to 8-day old soybean seedlings.

FIG. 1B: Wounded transformable soybean explant FIG. 1C: Co-cultivation with *Agrobacterium*. Soybean explants were co-cultivated with *Agrobacterium* for approximately 5 days FIG. 2A: Explants with formed leaf/shoot structures derived from a transformed primary leaf node. The explant has been inserted into the growing medium in an upward position so that the transformed cells are not in direct contact with the growing medium comprising the selection compound.

FIG. 2B: Separation of elongated shoots from the explants. After separation, the shoots were rooted individually.

FIG. 3A: Composite plant with a non-transgenic (wild-type) hypocotyl and epicotyl transgenic parts which are derived from the transformed plant cell. For obtaining this plant, meristematic tissue of a primary leaf node has been transformed. In contrast to the plants shown in FIG. 2B, the elongated shoots were not separated from the explant.

FIG. 3B: Transgenic shoot (containing DsRed gene) elongating from the primary leaf node region of a seedling explant on a hydroponic medium The following examples are only intended to illustrate the present invention. They shall not limit the scope of the invention in any way.

EXAMPLES

Example 1

Sterilization and Germination of Soybean Seeds

Soybean seeds were sterilized in a desiccator with chlorine gas, which was produced by adding 3.5 ml 12N HCl drop-wise into 100 ml bleach (5.25% sodium hypochlorite). After 24 to 48 hours, seeds were removed from the desiccator and stored in room temperature for a short period of time before use. For seed germination, approximately 30 to 50 seeds were plated on a solid seed germination medium in a PlantCon® container and grown under at 27° C. for 7 to 8 days.

Example 2

Preparation of *Agrobacterium* Cultures and Explants for Transformation

*Agrobacterium* cell cultures were prepared by streaking *Agrobacterium* (e.g., *A. tumefaciens* or *A. rhizogenes*) carrying the desired binary vector onto solid YEP growth medium containing an appropriate antibiotic, such as kanamycin or spectinomycin. They were grown in an incubator at 28° C. After approximately two days, one or several colonies are picked (with a sterile toothpick) and inoculated in 50 ml of liquid YEP medium with an appropriate antibiotic (kanamycin or streptomycin). They were then placed on a shaker and shaken at 200-250 rpm (28° C.) for about 24 hr or until an $OD_{660}$ between 1.0-1.5 was reached. Working *Agrobacterium* glycerol stocks were prepared by mixing an equal volume of *Agrobacterium* suspension and glycerol). Each 160-170 µl of *Agrobacterium* stocks were aliquot into a 200 µl Eppendorf tubes and then stored at −80° C. until use. The day before infecting explant with *Agrobacterium*, 100-150 µl of working *Agrobacterium* stock µl were pipette into 100-150 ml of YEP in a 400 ml centrifuge bottle. The centrifuge bottles were placed on a shaker and shaken overnight at 28° C. or until an $OD_{660}$ between 1.0 and 1.5 was reached.

On the day when transformation experiments were carried out, the *agrobacteria* were collected by centrifuging them at 5,000 g for 8 minutes. The pellets were re-suspended in a liquid co-cultivation medium to the desired density ($OD_{660}$=1.5) and placed at room temperature for at least 30 min before use.

The following table shows the composition of the liquid co-cultivation medium (pH 5.4).

| Ingredients | Concentration/Units |
|---|---|
| Gamborgs B5 Salts | 1/10 X |
| Sucrose | 30 g/L |
| MES Hydrated | 20 mM |
| Gamborg's Vitamins 1000X | 1 X |
| Kinetin | 5 uM |
| Giberellic Acid | 0.5 mg/l |
| Acetosyringone | 0.2 mM |

Explants for *Agrobacterium* infection were prepared by removing most of the hypocotyl, one cotyledon and all preformed leaves (including apical meristem) from the 7 to 8-day old seedling. After co-cultivation with the re-suspended *Agrobacterium* mixture for 30 minutes, the explants were transferred to petri plates and plated on a co-cultivation medium. They were grown in the dark at 25° C. for 5 days. (The explants plants might be 1 to 3 inches in length after the co-cultivation period).

The following table shows the composition of the co-cultivation medium (pH 5.4) used for the plates.

| Ingredients | Concentration/Units |
| --- | --- |
| Gamborgs B5 Salts | 1/10 X |
| Sucrose | 30 g/L |
| MES Hydrated 2-(N-morpholino) ethanesulfonic acid | 20 mM |
| Gamborg's Vitamins 1000X | 1X |
| Kinetin | 5 uM |
| Giberellic Acid | 0.5 mg/l |
| Acetosyringone | 0.2 mM |
| L-cysteine | 4.4 mM |
| Sodium Thiosulfate | 0.5 mM |
| DTT | 0.5 mM |

Example 3

Shoot Development

For shoot development, the *Agrobacterium* infected explants were transferred to Oasis™ wedges right after the co-cultivation period. Alternatively, the explants were first grown in a shoot induction media for 1-3 weeks before transfer to the wedges. The explants were placed vertically in the wedges with their residual hypocotyl part inserted into the wedges. The wedges were watered with a selection agent once or twice a week. (In the case where explants were infected with *Agrobacterium* harboring a construct that contains a mutated AHAS gene, they were watered with a solution that contains an imidazolinone herbicide as a selective agent).

When shoots became elongated from the infected primary leaf node region, they were separated from the seedling and rooted individually in Oasis™ wedges. The detached shoots were watered with a solution containing an imidazolinone herbicide once or twice a week. When the shoots become rooted, they were transferred to soil and grown to maturity in the greenhouse. Alternatively, the whole explants (seedlings), with the elongated shoots attached to them, were transferred to soil and grown to maturity in the greenhouse.

Example 4

Soybean cv. Williams82 seed germination, *Agrobacterium* preparation, explant preparation, and inoculation of *Agrobacterium* to explants were carried out as previously described. A construct that contains a mutated AHAS gene driven by a parsley ubiquitin promoter and a β-glucuronidase (GUS) gene driven by a parsley ubiquitin promoter, was delivered to soybean cells by *Agrobacterium*. After 5 days of co-cultivation, the *Agrobacterium*-infected explants were transferred to Oasis™ wedges with their hypocotyls inserted in the wedges. They were watered with a solution containing 1.5 uM Imazapyr once or twice a week. Leaf tissues from emerged shoots were collected and incubated in an x-gluc solution for detection of expression of GUS gene.

| Experiment | #Explants Infected with Agrobacterium | #Explants with leaf tissue showing expression of gus gene |
| --- | --- | --- |
| A | 50 | 2 |
| B | 50 | 2 |
| C | 70 | 1 |

Example 5

Soybean cv. Williams82 seed germination, *Agrobacterium* and explant preparation, and inoculation of *Agrobacterium* to explants were carried out as previously described. A construct that contains a mutated AHAS gene driven by a parsley ubiquitin promoter and a β-glucuronidase (GUS) gene driven by a parsley ubiquitin promoter, was delivered to soybean cells by *Agrobacterium*. After 5 days of co-cultivation, the *Agrobacterium*-infected explants were transferred to a shoot induction medium (SIM) containing 3 μM Imazapyr. After one week, the seedling explant was transferred to Oasis™ wedges with their hypocotyls inserted in the wedges. They were watered with a solution containing 1-2 μM Imazapyr and 1 mg/l IAA once or twice a week. Leaf tissues from emerged shoots were collected 2-4 weeks after and incubated in an x-gluc solution for detection of expression of GUS gene.

| Experiment | #Explants Infected with Agrobacterium | #Explants with leaf tissue showing expression of gus gene |
| --- | --- | --- |
| A | 75 | 19 |
| B | 100 | 30 |

Example 6

Soybean cv. Williams82 seed germination, *Agrobacterium* and explant preparation, and inoculations of *Agrobacterium* to explants were carried out as previously described. A construct that contains a mutated AHAS gene a gene coding for disease resistance was delivered to soybean cells by *Agrobacterium*. After 5 days of co-cultivation, 21 of the *Agrobacterium*-infected explants were transferred to Oasis™ wedges with their hypocotyls inserted in the wedges.

They were watered with a solution that contains 1-2 μM Imazapyr once or twice a week. 17 of the explants with their elongated shoots were transferred to the greenhouse and potted in soil. Leaf tissues were collected and analyzed by Taqman™ assay for the presence of AHAS gene. Among those analyzed, 3 were positive.

Example 7

Soybean cv. Williams82 seed germination, *Agrobacterium* and explant preparation, and inoculation of *Agrobacterium* to explants were carried out as previously described. A construct that contains a mutated AHAS gene driven by a parsley ubiquitin promoter, was delivered to soybean cells by *Agrobacterium*. After 5 days of co-cultivation, the *Agrobacterium*-infected explants were transferred to a shoot induction medium (SIM) containing 3 uM Imazapyr. After two weeks, the seedling explant was transferred to Oasis™ wedges with their hypocotyls inserted in the wedges. They were watered with a solution containing 1-2 uM Imazapyr and 1 mg/l IAA once or twice a week. Leaf tissues were collected and analyzed by Taqman™ assay for the presence of AHAS gene. A total of 70 explants were infected with *Agrobacterium*. 30 seedling explants were transferred to Oasis™ wedges. Among those analyzed, 5 were positive for the presence of AHAS gene.

Example 8

Soybean seed germination, *Agrobacterium* and explant preparation, and inoculations were carried out as previously described. A construct that contains a mutated AHAS gene and a gene coded for disease resistance was delivered to soybean cells by *Agrobacterium*. After 5 days of co-cultivation, the *Agrobacterium*-infected explants were placed in a shoot induction medium that contains Imazapyr as selection agent for 1-3 weeks. To promote shoot elongation, the seedling explant was transferred to Oasis™ wedges with their hypocotyls inserted in the wedges. Elongated shoots were separated from the explant and transferred to Oasis™ wedges for rooting. They were watered with a solution that contains 1-2 µM Imazapyr and 1 mg/l IAA once or twice a week. Rooted shoots were transferred to soil. Leaf tissues were collected and analyzed by Taqman™ assay for the presence of AHAS gene. Plants were grown to maturity in the greenhouse.

| Experiment | #Explants | #Positive events | Transformation Efficiency (%) | Genotype |
|---|---|---|---|---|
| A | 69 | 4 | 6 | Jake |
| B | 99 | 25 | 25 | Jake |
| C | 48 | 4 | 8 | Stoddard |

Example 9

Soybean seed germination, *Agrobacterium* and explant preparation, and inoculations were carried out as previously described. A construct that contains a mutated AHAS gene driven by a parsley ubiquitin promoter, was delivered to soybean cells by *Agrobacterium*. After 5 days of co-cultivation, the *Agrobacterium*-infected explants were placed in a shoot induction medium that contains Imazapyr as selection agent for 1-3 weeks. To promote shoot elongation, the seedling explant was transferred to Oasis™ wedges with their hypocotyls inserted in the wedges. Elongated shoots were separated from the explant and transferred to Oasis™ wedges for rooting. They were watered with a solution that contains 1-2 µM Imazapyr and 1 mg/l IAA once or twice a week. Rooted shoots were transferred to soil. Leaf tissues were collected and analyzed by Taqman™ assay for the presence of AHAS gene. Plants were grown to maturity in the greenhouse.

| Experiment | #Explants | #Positive events | Transformation Efficiency (%) | Genotype |
|---|---|---|---|---|
| A | 51 | 6 | 12 | Stoddard |
| B | 54 | 6 | 11 | Stoddard |
| C | 84 | 5 | 6 | Williams82 |

Example 10

Soybean cv. Williams82 seed germination, *Agrobacterium* and explant preparation, and inoculations were carried out as previously described. A construct that contains a mutated AHAS gene and a gene coded for disease resistance was delivered to soybean cells by *Agrobacterium*. After 5 days of co-cultivation, the *Agrobacterium*-infected explants were placed in a shoot induction medium that contains 3 µM Imazapyr. After 3-4 weeks, the meristem region of primary leaf node, with which a cluster of newly formed leaf or shoot structures) were separated from the epicotyls and transferred to Oasis wedges. They were watered with a solution that contains 1-2 µM Imazapyr and 1 mg/l IAA once or twice a week. Rooted shoots were transferred to soil. Leaf tissues were collected and analyzed by Taqman™ assay for the presence of AHAS gene. Plants were grown to maturity in the greenhouse.

| Experiment | #Explants | #Positive events | Transformation Efficiency (%) |
|---|---|---|---|
| A | 80 | 13 | 16.2 |
| B | 105 | 15 | 14.3 |
| C | 130 | 14 | 10.8 |
| D | 108 | 6 | 5.5 |
| E | 80 | 6 | 7.5 |

Example 11

Soybean cv. Williams82 seed germination, *Agrobacterium* and explant preparation, and inoculations were carried out as previously described. A construct that contains a mutated AHAS gene and a gene coded for disease resistance was delivered to soybean cells by *Agrobacterium*. After 5 days of co-cultivation, the *Agrobacterium*-infected explants were placed in a shoot induction medium that contains Imazapyr as selection agent for approximately 2 weeks. To promote shoot elongation, the seedling explant was transferred to Oasis™ wedges with their hypocotyls inserted in the wedges. Elongated shoots were separated from the explant and transferred to Oasis™ wedges for rooting. They were watered with a solution that contains 1-3 µM Imazapyr once or twice a week. Rooted shoots were transferred to soil. Leaf tissues were collected and analyzed by Taqman™ assay for the presence of AHAS gene. Plants were grown to maturity in the greenhouse.

| Experiment | #Explants | #Positive events | Transformation Efficiency (%) |
|---|---|---|---|
| A | 84 | 3 | 3.57 |
| B | 91 | 7 | 7.69 |
| C | 70 | 9 | 12.86 |
| D | 74 | 4 | 5.41 |
| E | 79 | 8 | 10.31 |
| F | 109 | 14 | 12.84 |
| G | 83 | 20 | 24.1 |
| H | 147 | 9 | 6.12 |

Example 12

Soybean cv. Willaims82 seed germination, *Agrobacterium* and explant preparation, and inoculations were carried out as previously described. A construct that contains a mutated AHAS gene and a second gene coded for herbicide tolerance was delivered to soybean cells by *Agrobacterium*. After 5 days of co-cultivation, the *Agrobacterium*-infected explants were placed in a shoot induction medium that contains Imazapyr as selection agent for approximately 2 weeks. To promote shoot elongation, the seedling explant was transferred to Oasis™ wedges with their hypocotyls inserted in the wedges. Elongated shoots were separated from the explant and transferred to Oasis™ wedges for rooting. They were watered with a solution that contains 1-3 µM Imazapyr once or twice a week. Rooted shoots were transferred to soil. Leaf tissues were collected and analyzed by Taqman™ assay for the presence of AHAS gene. Plants were grown to maturity in the greenhouse.

| Experiment | #Explants | #Positive events | Transformation Efficiency (%) |
| --- | --- | --- | --- |
| A | 87 | 6 | 6.9 |
| B | 81 | 5 | 6.17 |
| C | 125 | 3 | 2.4 |

The invention claimed is:

1. A method for producing a transgenic plant, comprising the steps of:
   a) providing a wounded transformable explant, comprising a hypocotyl or a portion thereof, at least one cotyledon, and wounded tissue selected from a group consisting of:
      i. wounded meristematic tissue of a primary or higher leaf node,
      ii. wounded meristematic tissue of the cotyledonary node; and
      iii. wounded epicotyl tissue;
   b) transforming cells of said wounded tissue with a polynucleotide comprising at least one plant expression cassette comprising a selectable marker gene;
   c) transferring said explant with transformed cells from step b) to a growing medium by inserting the hypocotyl, or portion thereof, of said explant with transformed cells from step b) into said growing medium comprising at least one selection compound for said selectable marker gene, wherein the explant is placed in an upward position in the growing medium;
   d) allowing said explant from step c) to form a shoot and/or allowing the shoot to elongate, wherein said shoot comprises plant cells comprising said polynucleotide comprising said least one plant expression cassette comprising said selectable marker gene; and
   e) producing the transgenic plant by either (1) regenerating the transgenic plant from said shoot without separating the shoot or (2) separating the shoot and then regenerating the transgenic plant from the separated shoot,
   wherein, in steps c) and d), the transformed plant cells of the explant are not in direct contact with the surface of the growing medium comprising the selection compound, and
   wherein the hypocotyl, or portion thereof, is not transformed with the polynucleotide comprising the at least one plant expression cassette.

2. The method of claim 1, wherein step b) is carried out by co-cultivating said explant with *Agrobacterium* comprising a T-DNA, said T-DNA comprising the polynucleotide comprising at least one plant expression cassette comprising a selectable marker gene.

3. The method of claim 1, wherein the explant in step a) is derived from a 6 to 10 day old seedling.

4. The method of claim 2, wherein the co-cultivation allows for transforming cells comprised by the wounded meristematic tissue so that a chimeric explant is obtained.

5. The method of claim 1, further comprising a step b1) of transferring said explant to a shoot induction medium and cultivating said explant on said shoot induction medium.

6. The method of claim 1, wherein step c) is carried out immediately after step b).

7. The method of claim 1, wherein, in step d), the explant is cultivated under ex vitro conditions after transferring said explant to a growing medium.

8. The method of claim 1 wherein step e) further comprises the steps of:
   e1) separating the elongated shoot obtained in step d) from the explant;
   e2) transferring the separated elongated shoot to a growing medium; and
   e3) regenerating a transgenic plant from said elongated shoot.

9. The method of claim 1, wherein the transgenic plant in step e) is regenerated without separating the elongated shoot from said explant.

10. The method of claim 1, wherein the growing medium of step c) is a hydroponic medium.

11. The method of claim 1, wherein the selectable marker gene is a mutated AHAS gene (acetohydroxyacid synthase gene) or a marker gene that confers resistance or increased tolerance to against the toxic effects imposed by D-amino acids.

12. The method of claim 11, wherein the selectable marker gene is a mutated AHAS gene, and wherein the selection compound is an imidazolinone herbicide.

13. The method of claim 1, wherein the plant is a dicotyledonous plant.

14. The method of claim 10, wherein the hydroponic medium is a formaldehyde or cellulose based foam.

15. The method of claim 11, wherein the selectable marker gene is a marker gene that encodes for a D-serine ammonialyase, a D-amino acid oxidase, or a D-alanine transaminase.

16. The method of claim 1, wherein the genus of the plant is selected from the group consisting of *Glycine, Medicago*, and *Phaseolus*.

17. The method of claim 1, wherein the plant is a soybean plant.

18. The method of claim 1, wherein the plant has developed flowers.

19. The method of claim 1, wherein the plant has developed seeds comprising the at least one plant expression cassette.

* * * * *